United States Patent
Lacy et al.

(10) Patent No.: US 11,605,462 B1
(45) Date of Patent: Mar. 14, 2023

(54) SYSTEM AND METHODS FOR HUMAN IDENTIFICATION OF INDIVIDUALS WITH COVID-19 UTILIZING DYNAMIC ADAPTIVE BIOMETRICS

(71) Applicant: Great Plain Technologies LLC, Pittston, PA (US)

(72) Inventors: Clifton R. Lacy, Highland Park, NJ (US); Warren S. Gifford, Monroe Township, NJ (US); David L. Turock, Fort Lauderdale, FL (US)

(73) Assignee: Great Plain Technologies, LLC, Pittston, PA (US)

( * ) Notice: Subject to any disclaimer, the term of this patent is extended or adjusted under 35 U.S.C. 154(b) by 0 days.

(21) Appl. No.: 17/565,668

(22) Filed: Dec. 30, 2021

(51) Int. Cl.
- *G16H 50/20* (2018.01)
- *G16H 50/30* (2018.01)
- *G16H 50/80* (2018.01)

(52) U.S. Cl.
CPC ............. *G16H 50/20* (2018.01); *G16H 50/30* (2018.01); *G16H 50/80* (2018.01)

(58) Field of Classification Search
CPC ......... G16H 50/20; G16H 50/30; G16H 50/80
See application file for complete search history.

(56) References Cited

U.S. PATENT DOCUMENTS

| | | | |
|---|---|---|---|
| 5,915,973 A * | 6/1999 | Hoehn-Saric | G09B 7/00 434/323 |
| 8,986,218 B2 | 3/2015 | DeLemos et al. | |
| 10,888,283 B1 | 1/2021 | Benjauthrit et al. | |
| 11,083,405 B1 * | 8/2021 | Lacy | A61B 5/746 |
| 11,253,490 B1 | 2/2022 | Levi et al. | |
| 2004/0229198 A1 * | 11/2004 | Boyd | G09B 7/00 434/236 |
| 2006/0115130 A1 * | 6/2006 | Kozlay | G06F 21/32 340/5.74 |
| 2011/0304465 A1 | 12/2011 | Boult et al. | |
| 2011/0314559 A1 * | 12/2011 | Jakobsson | H04L 9/3271 726/28 |
| 2012/0050685 A1 | 3/2012 | Bartlett et al. | |
| 2012/0078065 A1 | 3/2012 | DeLemos et al. | |
| 2017/0366546 A1 | 12/2017 | Bowles et al. | |
| 2019/0239790 A1 | 8/2019 | Gross et al. | |

(Continued)

OTHER PUBLICATIONS

Rui, Zhang, "A Survey on Biometric Authentication: Toward Secure and Privacy-Preserving Identification," IEEE vol. 7, 2019 (Year: 2019).*

(Continued)

*Primary Examiner* — John P Go

(74) *Attorney, Agent, or Firm* — DLA Piper (US) LLP

(57) ABSTRACT

Systems and methods for biometrically identifying an individual via a screening system for screening a subject for a response to neurophysiological stimuli as an indication for COVID-19, wherein the screening system is configured to capture biometric data associated with the subject during screening of the subject. The systems and methods provide the subject a neurophysiological stimulus selected for clinical manifestations of COVID-19, updating biometric template as necessary for individuals, and then determining whether an individual is the subject based on the updated biometric template and a response exhibited by the subject to the neurophysiological stimulus.

20 Claims, 13 Drawing Sheets

(56) References Cited

U.S. PATENT DOCUMENTS

| | | |
|---|---|---|
| 2019/0300034 A1 | 10/2019 | Molne et al. |
| 2020/0103967 A1 | 4/2020 | Bar Zeev et al. |
| 2021/0293827 A1 | 9/2021 | Winchester |
| 2021/0330259 A1 | 10/2021 | Liu et al. |
| 2022/0084672 A1 | 3/2022 | Hall |
| 2022/0240835 A1 | 8/2022 | Lacy et al. |
| 2022/0240836 A1 | 8/2022 | Lacy et al. |

OTHER PUBLICATIONS

Aguillon-Hernandez et al. "An odor identification approach based on event-related pupil dilation and gaze focus" Mar. 2015, International Journal of Psychophysiology 96(3):201-209.

Hornuss et al. "Anosmia in COVID-19 patients" 2020, Clin Microbiol Infect 26(10):1426-1427.

Hummel et al. "Screening of Olfactory Function with a Four-Minute Odor Identification Test: Reliability, Normative Data and Investigations in Patients with Olfactory Loss" 2009, Annals of Otology, Rhinology & Laryngology 110(10):976-981.

International Search Report and Written Opinion for PCT/US2021/045229 dated Sep. 20, 2021.

Nguyen et al. "Olfactory exploration: State of the art" 2016, European Annals of Otorhinolaryngology, Head and Neck diseases 133 2016:113-118.

Schneider et al. "Pupillary responses to intranasal trigeminal and olfactory stimulation" 2009, J Neural Transm (2009) 116:885-889.

Ono et al. "Autonomic Nerve Reaction by Taste Stimulus of the Recognition Threshold Density" 2017, Nano Biomedicine 9(2):50-54.

Sheen et al. "Evaluating the Onset, Severity, and Recovery of Changes to Smell and Taste Associated with COVID-19 Infection in a Singaporean Ppulation (the OVOSMIA-19 Trial): Protocol for a Prospective Case-Control Study" 2020, JMIR Res. Protoc. 9(12):324797.

Lemercier et al. "Pupillometry of taste: Methodological Guide-from acquisition to data processing-and toolbox for MATLAB" 2014, Quantitative Methods for Psychology 10.2:179-195.

Zahra et al. "Can Symptoms of Anosmia and Dysgeusia be Diagnostic for COVID-19?" 2020, Brain Behav. 10:301839. https://doi.org/10.1002/brb3.1839.

\* cited by examiner

SYSTEM AND METHODS FOR HUMAN IDENTIFICATION OF INDIVIDUALS WITH COVID-19 UTILIZING DYNAMIC ADAPTIVE BIOMETRICS

BACKGROUND

Accurately identifying the subjects that are being screened for various conditions and access control using screening systems is critical for several reasons. For example, accurately ascertaining the identity of the individual being screened assures the privacy of the subject's data, attributes data to the correct subject, and prevents unauthorized access from being granted to the system. Many different biometrics are used today for identification, including facial characteristics, fingerprint, hand shape, and retina scan. Many other body characteristics have been studied for their efficacy and identification such as the geometry of the ear. However, conventional systems that make use of static biometrics (e.g., a fingerprint) are particularly vulnerable to fraud or attack because static biometrics can be more easily spoofed or hacked. For example, a static facial recognition-based biometric might be simulated by a photograph or a computer-generated image. This issue is especially problematic for screening systems (e.g., public health screening systems) because users may be providing the system with substantial amounts of sensitive data that they would not want others to have access to. Further, the accuracy of the tracked data is of paramount importance in screening for particular conditions because compromised user credentials could lead to misattributed test results, which may in turn frustrate the ability for public health agencies to monitor the emergence and spread of conditions (e.g., COVID-19).

One technique for the robust, accurate identification of individuals is dynamic adaptive biometrics. Dynamic biometrics, such as eye motion patterns in response to visual stimuli and hand motions in response to task stimuli, are complex functions of time. They have been shown to be highly individualized and, thus, be useful for the characterization of each individual. Many biometrics in use today, such as fingerprints or facial scans, are chosen because they have a relatively small number (e.g., on the order of ten) of characteristic features that do not change over time, that is they are static. Although these characteristic features allow for individuals to be identified and the systems using the static features can be programmed to function in a relatively simple manner because the features are static, this also means the biometrics can be copied. Further, if an individual does undergo some change (e.g., via aging), then their biometrics may not be recognized. In contrast, measuring dynamic biometric properties of an individual can create a convenient and accurate source of data for identifying the individual. These biometric properties could be useful for other purposes, such as health screening, and can be obtained with simple equipment, such as a smart device.

Some screening systems (including systems that are described herein) can capture records of an individual's biometric patterns over time in order to identify variations in those biometric patterns, which can be indications of health issues. These screening systems establish typical behaviors and thresholds for changes in behavior, which can then be used to compare subsequent data against in order to identify deviations from the norms that could be indications of a condition. These systems can also pool data collected from several users in order to establish norms for populations. Accordingly, measured responses and/or behavior by an individual could be compared to population-wide norms and thresholds to determine when the individual's behavior deviates from the population. The data that is collected by the screening systems for identifying indications for conditions exhibited by subjects could also be used to distinguish between different individuals, i.e., for biometric identification. Comparing individual biometric results with other individuals to look for unique patterns allows the system to optimize the effectiveness and efficiency of the identification process. Further, the various types of data collected by the screening systems can be used in combinations with each other (on the order of hundreds of different measurements) to create powerful, dynamic adaptive biometric measures. Further, by measuring biometrics that are not easy to reproduce (e.g., biomechanical motion timing characteristics) the identification system is further strengthened. Additionally, due to the amount and comprehensive nature of the data that is collected for each subject, subjects' biometric templates could be updated each time an authentication procedure is performed by the screening system, thereby automatically incorporating changes exhibited by the subjects into the biometrics and reducing the identification error rate.

These measures are dynamic and adaptive in several ways: they are measuring dynamic biometric processes, the system automatically incorporates changes in behavior of individuals and the population, and the system can change what measures of the biometric processes are being used to optimize accuracy and efficiency.

Therefore, there is a need in the technical field for techniques to accurately and securely identify users in order to properly attribute test results and prevent unauthorized individuals from gaining access to other individuals' sensitive personal data. Further, using dynamic adaptive biometrics would be particularly advantageous in combination with the screening systems described herein that are configured to capture high dimensionality data for screening because this data could be additionally leveraged to generate dynamic adaptive biometrics for identification.

SUMMARY

There are provided systems and methods for identifying individuals using dynamic adaptive biometrics, particularly dynamic adaptive biometrics captured via systems for screening individuals for various conditions.

In some embodiments, there is provided a computer-implemented method for biometrically identifying an individual via a screening system for screening a subject for a response to neurophysiological stimuli as an indication for a condition, wherein the screening system is configured to capture biometric data associated with the subject during screening of the subject, the method comprising: receiving, by a mobile device, a biometric template associated with the subject, wherein the biometric template is configured to identify the subject, wherein the biometric template comprises a first subset of the biometric data for the subject captured by the screening system; determining, by the mobile device, whether to update the biometric template; in response to a determination to update the biometric template, generating, by the mobile device, an updated biometric template associated with the subject, wherein the updated biometric template is configured to identify the subject, wherein the updated biometric template comprises a second subset of the biometric data for the subject captured by the screening system, wherein the second subset of the biometric data differs from the first subset; and determining, by the mobile device, whether an individual is the subject based on the updated biometric template.

In some embodiments, there is provided a computer-implemented method for biometrically identifying an individual via a screening system for screening a subject for a response to neurophysiological stimuli as an indication for a condition, wherein the screening system is configured to capture biometric data associated with the subject during screening of the subject, the method comprising: receiving, by a mobile device, a biometric template associated with the subject, wherein the biometric template is configured to identify the subject, wherein the biometric template comprises a first subset of the biometric data for the subject captured by the screening system; determining, by the mobile device, whether to update the biometric template; in response to a determination to update the biometric template, generating, by the mobile device, an updated biometric template associated with the subject, wherein the updated biometric template is configured to identify the subject, wherein the updated biometric template comprises a second subset of the biometric data for the subject captured by the screening system, wherein the second subset of the biometric data differs from the first subset; and determining, by the mobile device, whether an individual is the subject based on the updated biometric template.

In some embodiments of the computer-implemented methods, the condition comprises COVID-19.

In some embodiments of the computer-implemented methods, the method further comprises in response to a determination that the individual is the subject based on the updated template: providing a stimulus to the subject; measuring, via a detector of the mobile device, a response of the subject to the stimulus; comparing, by a processor of the mobile device, the measured response to a reference; determining, by the processor, whether the subject demonstrates a diminished or an absent response to the stimulus according to whether the measured response differs from the reference by a threshold; and providing, by the processor, an alert according to whether the subject has the diminished or the absent response to the stimulus, wherein the alert comprises an intervention associated with COVID-19.

In some embodiments of the computer-implemented methods, the stimulus comprises at least one of an olfactory stimulus, an audio stimulus, or a visual stimulus.

In some embodiments of the computer-implemented methods, the stimulus comprises at least one of a trail-making test or a finger tapping test.

In some embodiments of the computer-implemented methods, the biometric data comprises at least one of eye movement data, response timing data, or accuracy data.

In some embodiments of the computer-implemented methods, the method further comprises voiding results of a screening test provided by the screening system in response to a determination that the individual is not the subject based on the updated biometric template.

In some embodiments of the computer-implemented methods, the method further comprises transmitting an alert to an authority in response to a determination that the individual is not the subject based on the updated biometric template.

In some embodiments of the computer-implemented methods, the method further comprises flagging the individual with a COVID-19 access control flag in response to a first determination that the individual is the subject based on the updated biometric template and a second determination that the individual has a diminished or an absent response to the neurophysiological stimulus based on the response exhibited by the subject.

In some embodiments, there is provided a system for screening a subject for a response to neurophysiological stimuli as an indication for COVID-19, the system comprising: a mobile device comprising: a processor, and a memory coupled to the processor, the memory storing instructions that, when executed by the processor, cause the mobile device to: receive a biometric template associated with the subject, wherein the biometric template is configured to identify the subject, wherein the biometric template comprises a first subset of the biometric data for the subject captured by the screening system; determine whether to update the biometric template; in response to a determination to update the biometric template, generate an updated biometric template associated with the subject, wherein the updated biometric template is configured to identify the subject, wherein the updated biometric template comprises a second subset of the biometric data for the subject captured by the screening system, wherein the second subset of the biometric data differs from the first subset; and determine whether an individual is the subject based on the updated biometric template.

In some embodiments of the systems, the memory stores further instructions that, when executed by the processor, cause the mobile device to: in response to a determination that the individual is the subject based on the updated template: provide a stimulus to the subject; measure, via a detector of the mobile device, a response of the subject to the stimulus; compare the measured response to a reference; determine whether the subject demonstrates a diminished or an absent response to the stimulus according to whether the measured response differs from the reference by a threshold; and provide an alert according to whether the subject has the diminished or the absent response to the stimulus, wherein the alert comprises an intervention associated with COVID-19.

In some embodiments of the systems, the stimulus comprises at least one of an olfactory stimulus, an audio stimulus, or a visual stimulus.

In some embodiments of the systems, the stimulus comprises at least one of a trail-making test or a finger tapping test.

In some embodiments of the systems, the biometric data comprises at least one of eye movement data, response timing data, or accuracy data.

In some embodiments of the systems, the memory stores further instructions that, when executed by the processor, cause the mobile device to: void results of a screening test provided by the screening system in response to a determination that the individual is not the subject based on the updated biometric template.

In some embodiments of the systems, the memory stores further instructions that, when executed by the processor, cause the mobile device to: transmit an alert to an authority in response to a determination that the individual is not the subject based on the updated biometric template.

In some embodiments of the systems, the memory stores further instructions that, when executed by the processor, cause the mobile device to: flag the individual with a COVID-19 access control flag in response to a first determination that the individual is the subject based on the updated biometric template and a second determination that the individual has a diminished or an absent response to the neurophysiological stimulus based on the response exhibited by the subject.

FIGURES

The accompanying drawings, which are incorporated in and form a part of the specification, illustrate the embodiments of the invention and together with the written description serve to explain the principles, characteristics, and features of the invention. In the drawings.

DESCRIPTION

Figure 1:
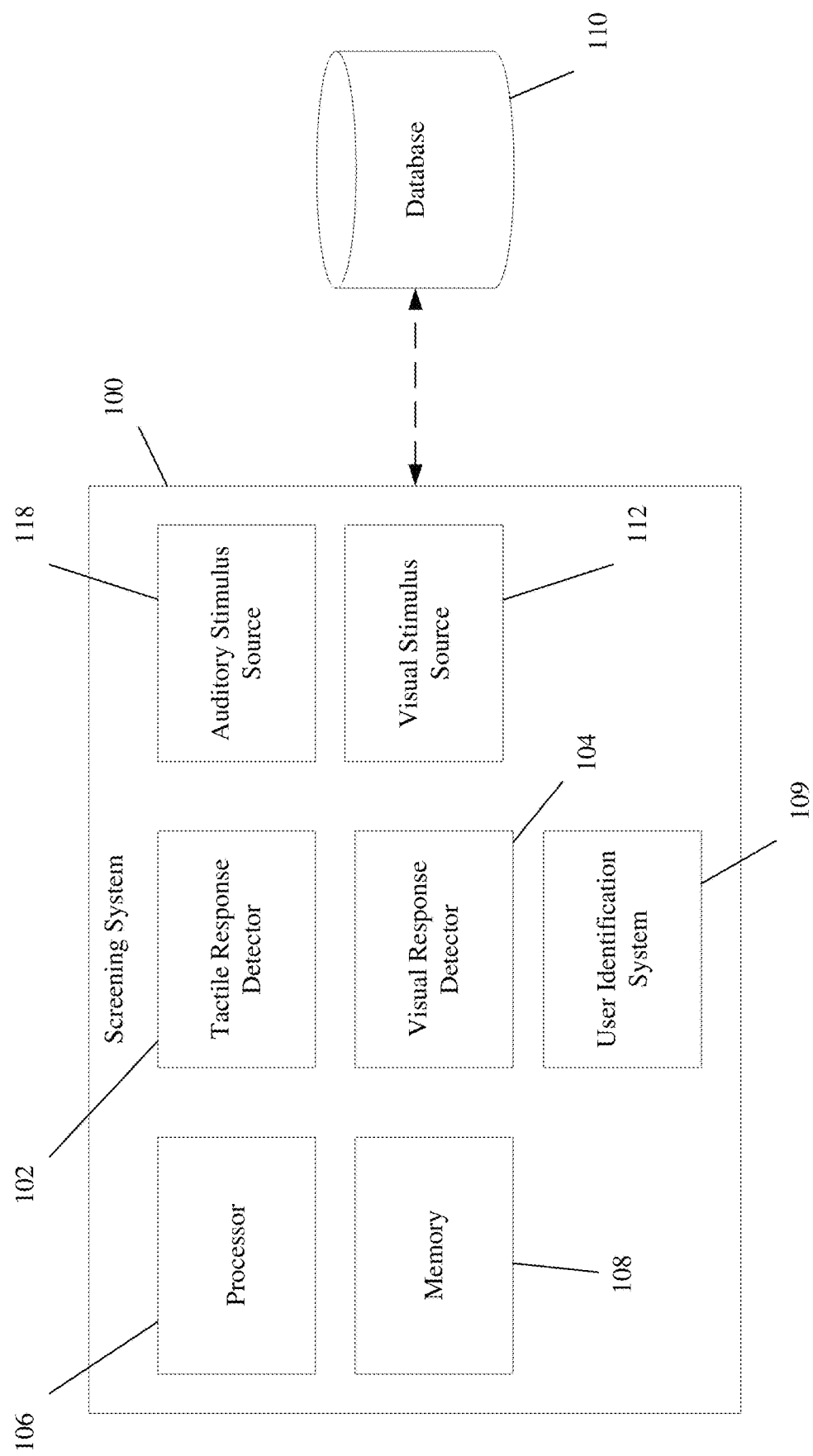
FIG. 1 illustrates a diagram of a screening system, in accordance with an embodiment.

As used herein, "COVID-19" means the infectious disease caused by the SARS-CoV-2 virus.

As used herein, "Long COVID" means symptoms associated with COVID-19 that persist weeks or months after the initial onset, such as brain fog.

As used herein, "brain fog" or "COVID-19 brain fog" means cognitive impairments resulting from COVID-19 that are characterized by an inability to concentrate, sustain attention, remember, or think or reason clearly.

As used herein, a "neuropathological condition" means a disease or physiological condition that exhibits or causes a neuropathological effect in a subject. Neuropathological conditions could include, for example, Long COVID or dementia.

As used herein, a "subject" refers to a human individual.

As used herein, a "neurophysiological stimulus" (collectively, "neurophysiological stimuli") means anything that is configured to elicit a somatic (i.e., voluntary) and/or autonomic (i.e., involuntary) response by a subject. Neurophysiological stimuli could include, for example, olfactory stimuli or visual stimuli. Neurophysiological stimuli could include both discrete stimuli (e.g., a single scent) or more complex combinations of stimuli (e.g., a trail-making test or a finger tapping test).

Generally described herein are various systems and processes for screening individuals for a variety of different conditions and generating dynamic adaptive biometrics from the captured screening data. The screening systems can provide subjects with various types of stimuli, measure the subject's somatic and/or autonomic response(s) to the stimuli, and assess whether the subject could have a particular condition based on measured responses. If the screening systems identify that the subjects are exhibiting a change in their normal response to the stimuli or that the subjects are exhibiting a response that deviates from a baseline or reference response to the stimuli, the screening systems could prompt the subject to seek medical evaluation, recommend further testing, recommend that the subject self-quarantine or isolate, or take a variety of other actions. Further, the screening systems can use the captured data to biometrically identify the subjects in order to, for example, ensure that the correct individual is taking the screening test. Accordingly, the systems and processes described herein can be used to identify subjects and screen the subjects for abnormal responses that may indicate a need for medical evaluation.

Systems for Screening Subjects

Described herein are systems and techniques for providing stimuli (e.g., neurophysiological stimuli) to a subject and assessing the subject's response thereto in order to screen for one or more neuropathologies associated with COVID-19. In some embodiments, the screening systems can be configured to supply olfactory stimuli to the subject and measure the subject's response (e.g., pupillary) thereto, such as is described in U.S. patent application Ser. No. 17/167,728, now U.S. Pat. No. 11,083,405, titled SYSTEMS AND METHODS FOR SCREENING SUBJECTS BASED ON PUPILLARY RESPONSE TO OLFACTORY STIMULATION, filed Feb. 4, 2021, which is hereby incorporated by reference herein in its entirety. In some embodiments, the screening systems can be configured to supply neurophysiological stimuli (e.g., audio stimuli or visual stimuli) to the subject and measure the subject's response (e.g., trail-making test accuracy) thereto, such as is described in U.S. patent application Ser. No. 17/528,417, titled SYSTEMS AND METHODS FOR SCREENING SUBJECTS FOR NEUROPATHOLOGY ASSOCIATED WITH A CONDITION UTILIZING A MOBILE DEVICE, filed Nov. 17, 2021, which is hereby incorporated by reference herein in its entirety. Further, the neurophysiological stimuli could take the form of various testing techniques that are provided to the subject, including eye tracking, trail-making, or eye-hand coordination testing techniques.

In one embodiment, a screening system 100 can include a visual stimulus source 112, a tactile response detector 102, and a visual response detector 104. The visual stimulus source 112 can include a standalone display screen or a display integrated into another device (e.g., a display of a smartphone). In one embodiment, the visual stimulus source 112 and the tactile response detector 102 can be integral to each other. For example, the visual stimulus source 112 and the tactile response detector 102 can be embodied as a touchscreen (e.g., a capacitive touchscreen). In one embodiment, the visual response detector 104 can include a camera or an image sensor. The visual response detector 104 can have sufficient resolution and other characteristics necessary to be able to detect the movements of a subject's eyes or portions thereof (e.g., the pupil) when positioned within a threshold distance to the subject.

The screening system 100 can be programmed or otherwise configured to provide a visual stimulus to a subject and track, monitor, or record the subject's response to the visual stimulus. Based on the subject's tracked response to the visual stimulus, the screening system 100 can be programmed or otherwise configured to make a determination as to whether the subject has findings compatible with a neuropathological condition, such as Long COVID or dementia. The visual stimulus provided to the subject could include a series of dots or patterns, icons, alphanumeric characters, or any other markers that can be visually identified and tracked by subjects. In various embodiments, the visual stimulus or portions thereof can move across the visual stimulus source 112, disappear and/or appear at various points on the visual stimulus source 112, change color, change shape, change visual perspective (e.g., rotate), and otherwise change in visually detectable manners. The screening system 100 can track a variety of different types of responses by a subject to the stimulus, including, for example, ocular responses, physical responses, or autonomic responses by the subject. In one embodiment, the screening system 100 can be configured to track eye movements by the subject in response to movements or changes by the visual stimulus. In another embodiment, the screening system 100 can be configured to track the ability of the subject to perform a trail-making test. As noted above, a trail-making test is a timed measurement of a subject's ability to connect numbers, letters, or other visual markers in a particular order (e.g., numerical or alphabetical order). A trail-making test can further task the subject with connecting the visual markers in a variety of different manners (e.g., in a forward, a backward, or an alternating fashion). The screening system 100 can track the subject's response(s) to the visual stimulus via the tactile response detector 102, the visual response detector 104, or a combination thereof depending upon the particular response being tracked thereby. For example, in embodiments where the response being tracked is the subject's eye movements, the screening system 100 can utilize the visual response detector 104 to track the characteristics of the subject's eyes. As another example, in embodiments where the response being tracked is the subject's ability to perform a trail-making test, the screening system 100 can utilize the tactile response detector 102 to track the subject's response to the trail-making test.

The visual response detector 104 could include standalone sensing devices or be incorporated into another device (e.g., a mobile device 122, as in the embodiments shown in FIGS. 2 and 3) or system. Further, in some embodiments, the visual response detector 104 could include one sensor or a set of sensors (i.e., a sensor assembly). The screening system 100 can be configured to execute various processes, such as those described below, to screen individuals based on their response or responses to stimuli provided by the screening system. In one embodiment, the screening system 100 can further include a processor 106 coupled to a memory 108 for storing data, including logic or instructions embodying processes to be executed by the processor.

The visual response detector 104 can be configured to capture images or video of a subject in sufficient detail such that the subject's eye movement response to the visual stimulus can be measured and, thus, quantified. In other words, the visual response detector 104 can be configured to capture images or video in a sufficiently high resolution and with sufficient clarity such that image processing algorithms can identify the subject's eyes (or portions thereof, such as pupils) and measure changes associated therewith. In various embodiments, the ocular response measured by the visual response detector 104 could include a change in the size (e.g., diameter or area) of the subject's pupil or pupils, timing information (e.g., hesitancy or delay in the pupil's movement), and other pupillary parameters. For example, the visual response detector 104 could be used to take a first measurement of a characteristic of the subject's eyes and take a second measurement of the characteristic after the subject has been provided the visual stimulus or after the initially provided visual stimulus has been changed by the screening system 100 (e.g., has moved, disappeared and reappeared at a different location on the visual stimulus source 112, changed in shape, or changed color). Accordingly, the subject's response to the visual stimulus could include the difference between the first and second measurements of the ocular characteristic.

In one embodiment, the screening system 100 could further include an auditory stimulus source 118. The auditory stimulus source 118 can be used to deliver instructions, produce audio signals for tapping cadence, be an element of the stimulus, or provide distractions as necessary for the testing.

The screening system 100 can be embodied as a variety of different objects, devices, or systems. In one embodiment, the screening system 100 could include a mobile device (e.g., a smartphone) and the processes executed thereby could include an app. In this embodiment, the screening system 100 could be beneficial by allowing individuals to self-screen for a particular condition or set of conditions using their own mobile device. In some embodiments, the visual response detector 104 could be embodied as an accessory or dongle that is connectable (either wirelessly or via a wired connection) or attachable to the mobile device. In other embodiments, the visual response detector 104 could include the onboard camera of the mobile device. Other embodiments could be suitable for screening individuals for entry to potentially crowded locations (e.g., schools, airports, or stadia). In one such embodiment, the screening system 100 could include a kiosk or station that includes the visual stimulus source 112 for providing the visual stimulus to subjects within the kiosk and the tactile response detector 102 and/or visual response detector 104. In this embodiment, the screening system 100 could be beneficial by allowing individuals to be screened for potential abnormalities (e.g., such as those associated with Long COVID or COVID-19 generally) prior to being permitted entry into a location. An abnormal response could be used as one of the tools to decide whether individuals should be permitted access to a venue, or require additional screening, thereby potentially avoiding significant adverse consequences (e.g., disease transmission events).

The screening system 100 can further include or be communicably connected to a database 110. The database 110 could include a local database 204 and/or a remote database 206, as described below. In one embodiment, the database 110 could be stored locally (i.e., in the memory 108). In another embodiment, the database 110 could be remote from the screening system 100. In this embodiment, the database 110 could be stored in a cloud computing storage system (e.g., Amazon Web Services), a remote server, and other such remote systems. The database 110 can be configured to store information including user parameters and settings, such as the user's previously calibrated responses. The user parameters could be embodied as a user profile, for example. The user parameters could include previously recorded values or measurements associated with the response measured by the screening system 100. The recorded parameters can be used to define a characterized or default response by the subject to the stimulus, which can in turn be used by the screening system 100 to determine when the subject's measured response deviates from this characterized or default response by the subject. Accordingly, the screening system 100 can determine when there has been a change in the patient's response to the stimulus, which could indicate that the patient has a condition that is screened by the screening system 100. The characterized or default response could be used to define various thresholds or ranges that could be used to determine whether the subject has passed or failed the screening. Accordingly, the screening system 100 can be configured to take measurements (e.g., via the visual response detector 104 and/or tactile response detector 102) associated with the subject's response to the stimulus, retrieve a user profile associated with the subject (e.g., from the database 110), and determine whether the subject has passed or failed the screening based on a comparison between the measurements of the response and the user profile parameters or a reference. For example, the screening system 100 can be configured to provide a trail-making test to the subject and measure the subject's response (i.e., the ability to properly track the moving visual stimulus) thereto. If there is a significant deviation from the subject's ability to perform the trail-making test relative to a reference or baseline (e.g., the stored, pre-characterized performance on the trail-making test associated with the subject or a universal characterized response), then the subject may be suffering from a neuropathological condition. Accordingly, the screening system 100 could prompt the subject regarding the need for medical evaluation (such as a physician checkup and/or testing including COVID-19 test) and/or suggest that the individual take corresponding appropriate precautions (e.g., self-quarantine or isolation). Conversely, if there is no significant deviation from the subject's ability to perform the trail-making test as compared to the reference or baseline, then the subject may not be suffering from such a neuropathological condition. Accordingly, the screening system 100 could take no action. In some embodiments, the screening system 100 can further record the subject's response(s) to the provided visual stimulus. The recorded responses could be used to further characterize the subject's baseline response characteristics, aggregated with records of other subjects (e.g., in the database 110) to further characterize universal or population-wide response characteristics, and so on.

The screening system 100 can further be configured to account for various secondary factors and be calibrated for each individual subject. For example, the screening system 100 may need to be calibrated to determine the baseline or expected response characteristics (e.g., eye movement hesitancy or degree of dilation in response to various visual stimuli or the sequence of objects the subject's eyes focus on) exhibited by the subject. Once the baseline or expected response characteristics are determined, subject measurements of those characteristics by the screening system 100 can be used to distinguish between potential neuropathological conditions and other abnormalities.

In one embodiment, the screening system 100 can be configured to determine the amount of light in the patient's environment (e.g., via the visual response detector 104) and, accordingly, account for the amount of light employed to determine the subject's response to the screening. The amount of ambient or environmental light can be an important factor because it can affect the ability of the subject's eyes to properly identify and distinguish between various visual stimuli, the contraction and dilation of the subject's pupils, and so on. In particular, a brightly lit ambient environment could decrease the pupil opening and, because the pupil is constricted, it may not dilate normally in response to particular visual stimuli. Conversely, in a dimly lit ambient environment, it may be more difficult for the subject's eyes to track the movement of the visual stimuli, or the screening system 100 may be unable to properly detect the subject's ocular response characteristics to the visual stimuli. Thus, in some embodiments, the screening system 100 can measure the amount of environmental light and recommend or effect adjustments for appropriate screening, such as blocking environmental light. In some embodiments, the screening system 100 can additionally be configured to control the amount of light in the test environment, such as by activating or controlling lights in the test environment.

In one embodiment, the screening system 100 could be configured to determine whether the subject has certain conditions, whether preexisting or temporary, that could affect its measurements. For example, the screening system 100 could automatically detect the presence of various indicators (e.g., cataracts), retrieve patient information (e.g., electronic medical records) from a database, or prompt the user to enter such information. This information is important because some indicators (such as cataracts) could affect pupillary response. Pupillary responses may be affected in different ways by different indicators. Thus, in some embodiments, the screening system 100 could be configured to detect and differentiate among such indicators. The screening system 100 could be configured to incorporate the presence of these indicators into the determination of the likelihood that the decrease or lack of ocular response is related to the tracked conditions. In addition, the screening system 100 could be configured to recommend additional screenings in the event that more determinations or more time would be advantageous in achieving a successful screening.

In some embodiments, the screening system 100 could be configured to account for a variety of other events or subject-specific or environmental conditions. For example, the screening system 100 could be configured to detect when the user was startled at the time of the test (e.g., due to a loud sound or bright flash) and adjust environmental conditions or recommend that the subject be retested. In one implementation, the screening system 100 could ask the subject one or more questions, such as "Are you currently suffering from a headache or a lack of sleep?", prior to beginning the screening test and act accordingly based on the subject's responses (e.g., recommending that the test be postponed). As another example, the screening system 100 could be configured to detect (e.g., via the visual response detector 104) whether there was any motion within the subject's field of vision that could have distracted the subject.

All of the various data associated with the subject that are discussed above, such as the subject's amount of ocular response characteristics at various lighting levels, the subject's response to various tests (e.g., accuracy or timing in performing trail-making tests), and so on, could be stored in a user profile associated with the subject. As discussed above, this data can be stored by and/or retrieved by the screening system 100 (e.g., from the database 110) at the time of the screening test to assist in the determination of positive or negative screening results.

Figure 2:
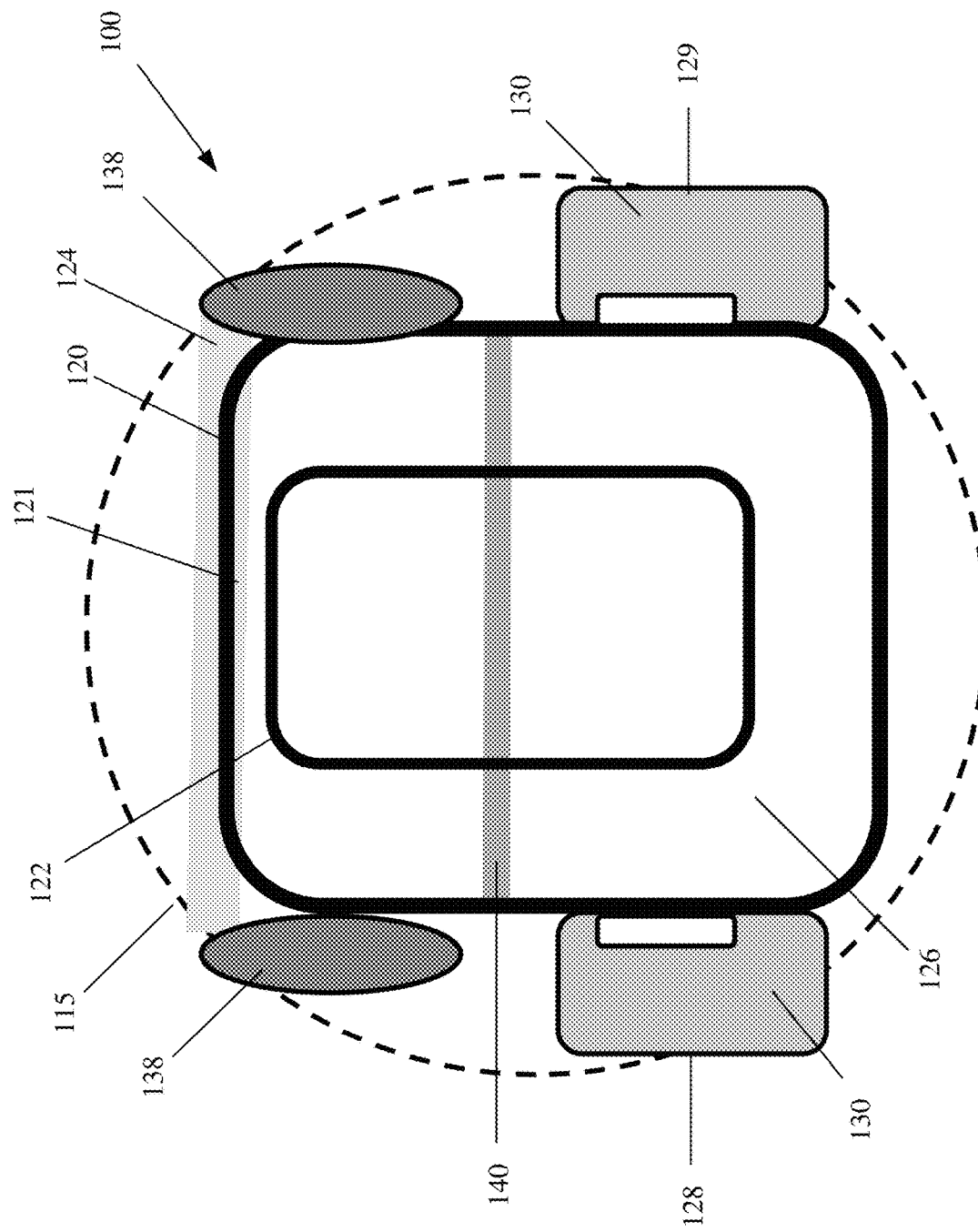
FIG. 2 illustrates a schematic diagram of a first embodiment of the screening system of FIG. 1.

One embodiment for the screening system 100 is shown in FIG. 2. In this embodiment, the screening system 100 could include a headpiece 120 that can be worn on the head 115 of the subject. In the illustrated embodiment, the headpiece 120 includes a holder 121 that is configured to hold a mobile device 122 (e.g., a smartphone or another smart device) that includes a visual response detector 104 (e.g., a camera). The holder 121 can be configured to hold the mobile device 122 such that the visual response detector 104 is oriented towards the subject's face when the headpiece 120 is worn by the subject. The mobile device 122 executing the app can be used to guide the subject through the screening steps with audio, images, text, or combinations thereof. Accordingly, in one implementation, users could place their mobile device 122 in the holder 121, and the mobile device can in turn execute an app stored thereon that performs the screening test, as described herein. In another embodiment, the detector 104 could be integral to the headpiece 120. The headpiece 120 can include one or more straps 124 or other securement devices for securing the headpiece to the subject's head 115 and keep the mobile device 122 in a fixed relationship to the subject's face.

In one embodiment, the headpiece 120 could define a partially or fully enclosed chamber 126 that is configured to provide a fixed environment suitable for the screening test for the subject. The headpiece 120 could further include an air inlet 128 (which can further include a filter 130, such as a P100 filter) and a corresponding outlet 129 for allowing the subject to exhale. The screening test could be activated manually by the subject or automatically by the screening system 100 (e.g., by the software app running on a mobile device 122). In still other embodiments, the headpiece 120 could include earphones 138 to control or reduce environmental noise and direct sounds from the mobile device 122 or sensor to the subject. Such embodiments can be beneficial because they provide a controlled environment for the performance of the screening test, which can increase reliability of the results.

Figure 3:
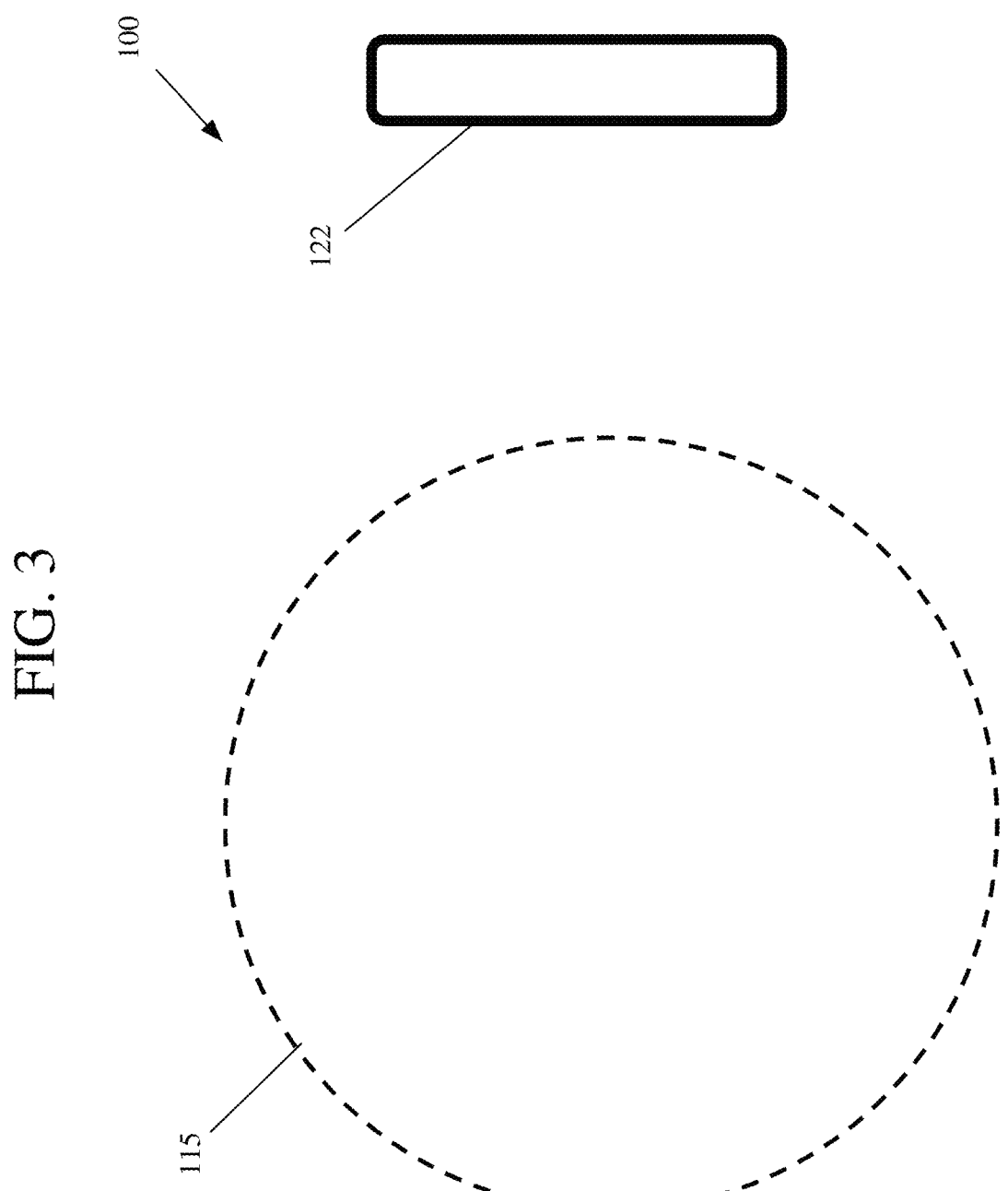
FIG. 3 illustrates a schematic diagram of a second embodiment of the screening system of FIG. 1.

Another embodiment of the screening system 100 is shown in FIG. 3. In this embodiment, rather than using the headpiece assembly described above with respect to FIG. 2, the subject could instead hold their mobile device 122 in close proximity to his or her face (or rest the mobile device 122 in an appropriate location). In this embodiment, the visual response detector 104 could include the onboard camera of the mobile device 122, and the tactile response detector 102 could include the capacitive touchscreen thereof. In this embodiment, the relationship between the subject's head 115 and the mobile device 122 is not fixed, so the mobile device (or the software app executed thereby) can therefore be configured to compensate for motion of the subject relative to the mobile device. Such an embodiment can be beneficial because of its ease of use. In particular, such an embodiment does not require a substantial number of components or for the subject to wear a head assembly or otherwise be within a fixed environment.

Figure 4:
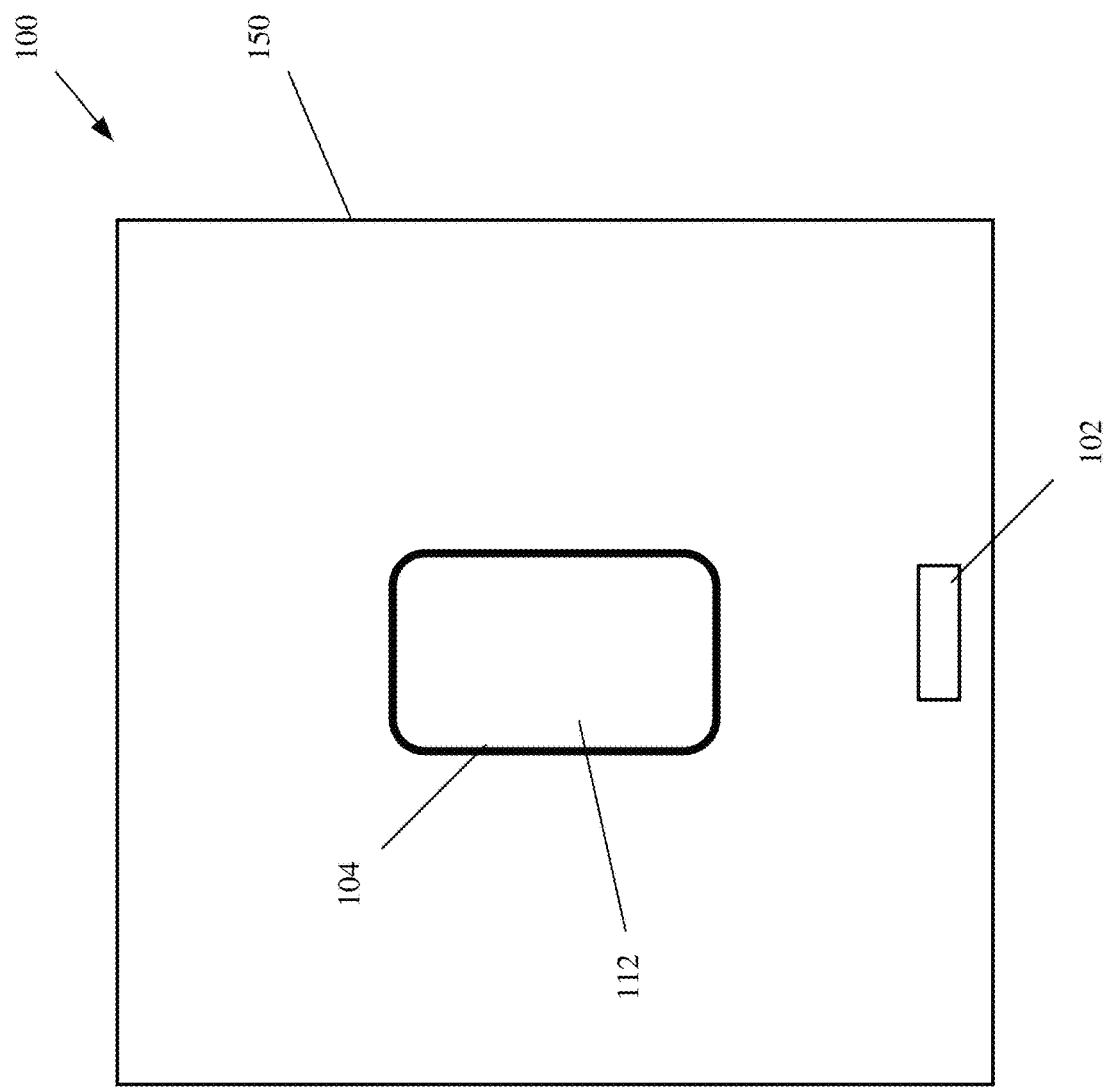
FIG. 4 illustrates a schematic diagram of a third embodiment of the screening system of FIG. 1.

Yet another embodiment of the screening system 100 is shown in FIG. 4. In this embodiment, the screening system 100 is embodied as a high-throughput system that could be suitable for screening at airports, stadia, and so on. In particular, this embodiment of the screening system 100 can include an enclosure 150 into which the subject can enter. The enclosure 150 could be an enclosure that is environmentally controlled, for example. The enclosure 150 could include a complete or partial enclosure (e.g., from the waist up). In such an embodiment, the subject enters the enclosure 150 and faces the visual stimulus source 112, which can further include the tactile response detector 102 (e.g., a capacitive touchscreen). As noted above, the visual response detector 104 could include a camera or an image sensor, for example. The visual stimulus source 112, visual response detector 104, and/or tactile response detector 102 could be positioned on a wall of the enclosure at a height suitable for visualizing individuals' faces and/or being readily reached by the individuals, for example, or at adjustable heights to optimize the relationship to the user. The visual stimulus source 112 could provide appropriate instructions to the subject (e.g., where to stand), what information to provide to the screening system 100 (e.g., whether the subject has any relevant information that may inform results of screening), or when to exit. The visual stimulus source 112, visual response detector 104, and/or tactile response detector 102 could include a smart device or a specialized sensor apparatus. The visual stimulus source 112, visual response detector 104, and/or tactile response detector 102 could be integral to or otherwise located within the enclosure 150.

Figure 5:
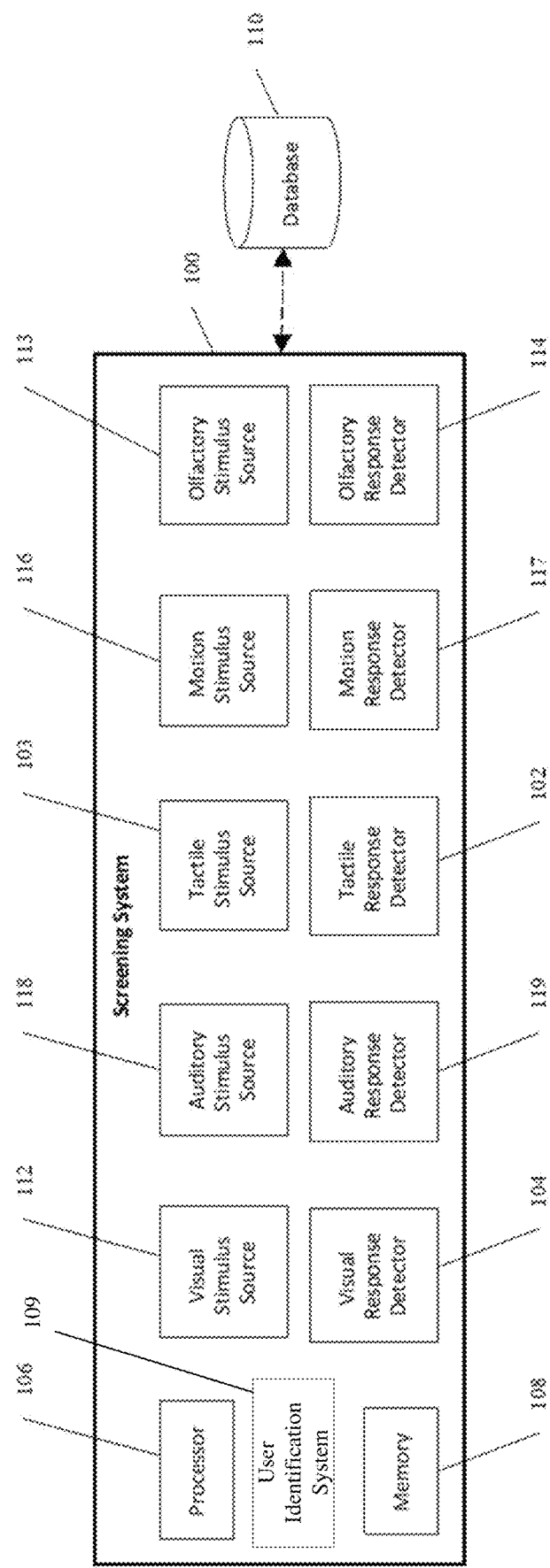
FIG. 5 illustrates a diagram of another embodiment of the screening system.

Another embodiment of the screening system 100 is shown in FIG. 5. In this embodiment, the screening system 100 could be embodied as a mobile device (e.g., a smartphone). This embodiment uses emerging capabilities of mobile devices to communicate more effectively with people, especially those with varying disabilities, such as hearing, motion and visual challenges, and for additional screening capabilities. In this embodiment, the screening system 100 is configured to provide a variety of different stimuli to the subject and detect the responses by the subject thereto. In particular, the screening system 100 can include a visual stimulus source 112, an auditory stimulus source 118, a visual response detector 104, and a tactile response detector 102, as described above. In this embodiment, the screening system 100 can further include one or more of an auditory response detector 119, a tactile stimulus source 103, an olfactory stimulus source 113, a motion stimulus source 116, a motion response detector 117, and an olfactory response detector 114, including any combination thereof. The auditory response detector 119, such as a microphone, is configured to detect and measure speech and other sounds from the subject, such as verbal responses, slurring of speech, heart beats, and bodily noises. In some embodiment, the auditory response detector 119 can further be configured to detect and measure potentially interfering sounds from the environment. The tactile response detector 102 is configured to detect and measure details of touch, such as, how hard a subject is pressing, how many fingers are touching the detector, details of motion, and uneven touch pressure such as from a tremor. The tactile stimulus source 103 is configured to create the impression of response to touch, such as depressing a virtual key by a subtle motion. The motion stimulus source 116 is configured to generate small motions, such as vibrations, which can be used to assess the ability to detect motion stimuli as well as give feedback to a subject, such as used to get attention when a smart phone is in silent mode. The screening system 100 can further be programmed or otherwise configured to perform speech-to-text translation (e.g., via software or an app executed by the processor 106) to detect and measure the appropriateness and accuracy of verbal responses derived from the speech of the subject. The motion response detector 117, such as an accelerometer, is configured to detect and measure changes in motion exhibited by the subject, such as tremors, startle responses, uneven motions (e.g., due to Parkinson's and other causes), and heartbeats. The method can include other stimuli and detectors, such as electrical stimuli and the associated detectors. The olfactory stimulus source 113 is configured to generate an olfactory stimulus and an olfactory stimulus detector 114 that is configured to detect and measure the same, such as is disclosed in U.S. patent application Ser. No. 17/167,728, titled SYSTEMS AND METHODS FOR SCREENING SUBJECTS BASED ON PUPILLARY RESPONSE TO OLFACTORY STIMULATION, filed Feb. 4, 2021, which is hereby incorporated by reference herein in its entirety.

In some embodiments, the screening system 100 can include a user identification system 109 that is configured to determine whether the individual interacting with the screening system 100 (e.g., attempting to take a screening test) is the correct user or one of the correct users associated with the screening system 100. The user identification system 109 could be configured to make use of dynamic adaptive biometrics, such as are described below.

As noted above, in one embodiment, the screening system 100 can be embodied as a mobile device 122. In other embodiments, the screening system 100 could be embodied as a combination of devices and/or systems that are communicatively coupled. For example, the screening system 100 could include a mobile device 122 that is coupled to a remote computing system (e.g., a server or a cloud computing system). In such embodiments, various steps, aspects, or techniques described above can be collectively executed by or between the devices and/or systems.

Neurophysiological Stimuli & Testing Techniques for Screening Systems

As described above, the various embodiments of the screening system 100 can be configured to provide a subject with a variety of different neurophysiological stimuli in order to assess the subject's response(s) to the stimuli and thereby determine whether the subject is indicated for the particular condition being screened. In some embodiments, the screening system 100 can provide a singular neurophysiological stimulus, such as an olfactory stimulus. In some embodiments, the screening system 100 can provide a more complex neurophysiological stimulus or a combination of neurophysiological stimuli, such as a trail-making test or a finger tapping test. In embodiments where the screening system 100 is providing neurophysiological stimuli embodied as a test (e.g., a trail-making test or a finger tapping test), the neurophysiological stimuli could be provided via the visual display source 112 (e.g., a display screen). In embodiments where the screening system 100 is at least partially embodied as a smartphone app, the neurophysiological stimuli could be provided as graphical elements displayed via the app on a subject's smartphone. In order to further illustrate the concepts behind these tests and the highly dimensional data gathered thereby, four examples of these tests are discussed below.

One test that can be provided by various embodiments of the screening system 100 is a pupil dilation test. Pupillary dilation is an autonomous response to many different kinds of stimuli, including light, a variety of drugs, interest in the subject of attention or arousal, sexual stimulation, uncertainty, decision conflict, errors, or increasing cognitive load or demand. Lack of pupil dilation in response to smell or taste is a useful indicator of COVID-19 infection. Therefore, some embodiments of the screening system 100 could be configured to test for pupillary dilation as at least one of the mechanisms for screening subjects for COVID-19. Some embodiments of screen systems 100 that are configured to measure pupillary response in subjects are described above and in U.S. Pat. No. 11,083,405, which is incorporated by reference above. However, pupillary dilation response profiles also vary from individual-to-individual due to genetics, environmental conditions, and age. Therefore, the pupillary dilation data captured by the screening system 100 for screening purposes could additionally be used for biometric identification of the subject.

An individual's pupillary response to a stimulus can produce several different measures and has many distinctive characteristics that differ among individuals, which thus allows pupillary response data to be used for biometric identification. In particular, an individual's pupil size begins at some initial value depending on the previous environment conditions. For example, if the beginning environment includes a bright light, then the pupil likely cannot contract anymore and will not respond to other mild stimuli. Because the pupil responds to so many different stimuli, including the cognitive state of the individual, the starting value is not completely determined solely by the controllable and observable environmental conditions. This makes the initial pupillary dilation level potentially different for each test for the same individual.

Figure 6:
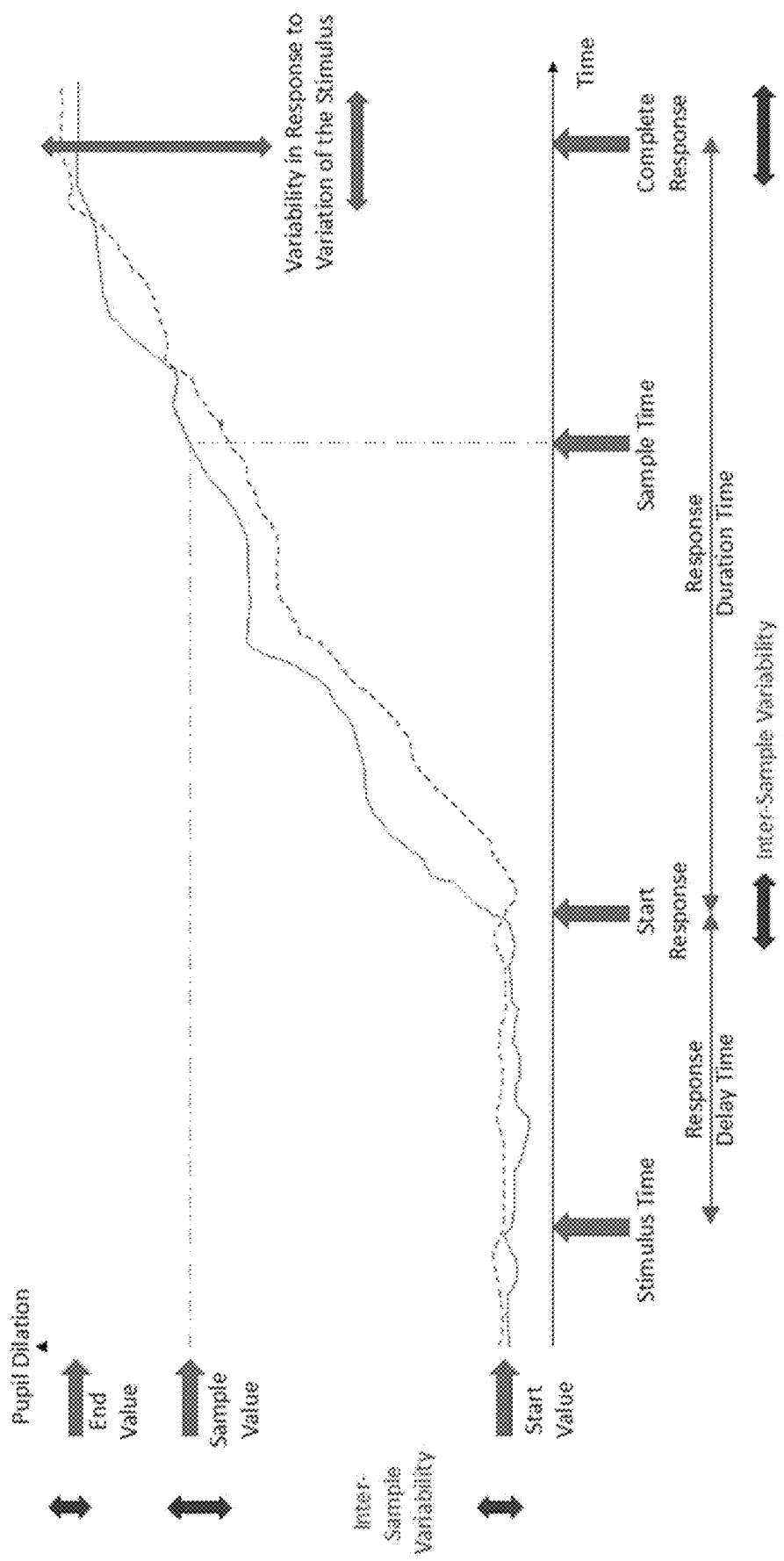
FIG. 6 illustrates a graph of pupillary response data for a subject, in accordance with an embodiment.

In some embodiments, the screening system 100 can be configured to provide a stimulus (e.g., light, smell, sound, images, or cognitive loads) to the subject and measure (e.g., via the visual response detector 104) the subject's pupillary response thereto. In one embodiment, the stimulus is introduced without warning to the subject. FIG. 6 demonstrates a characterized pupillary response for an illustrative subject. As can be seen in FIG. 6, once the stimulus has been provided to the subject, there is a delay until the pupillary response begins. The delay is dependent on the subject's initial pupillary state (e.g., degree of initial pupillary dilation) and the type of stimulus provided. Further, the pupillary delay varies by individual. There is some individual variability in the delay even for apparently identical conditions. After the delay period, the pupil then dilates or contracts over time. Once again, the rate and degree of the pupillary contraction depends on the initial pupillary state and the type of stimulus provided. The shape and duration of the dilation or contraction depends on the previous factors, and is characteristic of the individual. Further, one or more measurements of the pupil state can be taken based either on the time since the response started or when it attains a particular value. Unless there are any changes in the testing conditions (e.g., additional stimuli or changes in the environment), the pupil completes the adjustment. The length of time for the pupillary dilation and the end value (i.e., final pupillary diameter) are also distinctive for the individual.

In sum, multiple different types of pupillary response data (e.g., the initial pupillary delay, the rate of pupillary contraction, the degree of pupillary contraction, length of time for the pupillary dilation, and final pupillary diameter) could be used for biometric identification. Because multiple different biometric measures can be extracted from the subject's pupillary response data, the pupillary response data has a high degree of dimensionality. Even under the same conditions, there can be variations in each of these values for an individual.

Another test that can be provided by various embodiments of the screening system 100 is an eye tracking test. Eye motions are both autonomic and somatic, i.e., they have both independent and controllable components. Eye motion data can be indicative for a variety of different conditions, including conditions that impair cognitive functions (e.g., dementia). Therefore, some embodiments of the screening system 100 could be configured to measure eye motion as at least one of the mechanisms for screening subjects for various conditions. However, eye motions are also complex and distinctive. Therefore, the eye tracking data captured by the screening system 100 for screening purposes could additionally be used for biometric identification of the subject.

An individual's eye motion response to a stimulus can produce several different measures and has many distinctive characteristics that differ among individuals, which thus allows eye motion data to be used for biometric identification. Further, vision is open to stimulation and manipulation. For example, when scanning a scene the eyes initially move rapidly, then stay on a fixed point for some time, and then move to another point, on the order of three times per second. The eyes then repeat this process to scan the whole scene. However, the fixed points are not necessarily the objects within the scene or are in a particular sequence with respect to each other. Accordingly, there are four basic types of eye movements: saccades, smooth pursuit movements, vergence movements, and vestibulo-ocular movements. Saccades are rapid, ballistic movements of the eyes that abruptly change the point of fixation, and there are at least 9 different types. There are several reasons for saccades. The portion of the retina with highest resolution, the fovea, is quite small, so the eye needs to move to areas for a more detailed investigation (e.g., scanning a scene for interesting and important features). When concentrating on a particular area, the receptors lose sensitivity, and the eye needs to move away and then back again to the maintain focus on the area. Smooth pursuit movements are slower and track a moving object or changing subject of focus, such as reading. Vergence movements allow each eye to focus the fovea on objects at a particular distance. Vestibulo-ocular movements allow the eyes to compensate for movement of the head. All of these different types of eye movements vary from individual-to-individual.

Figure 7:
FIG. 7 illustrates a diagram of an eye tracking test, in accordance with an embodiment.

In some embodiments, the screening system 100 can be configured to provide a stimulus (e.g., an image or text) to the subject and measure (e.g., via the visual response detector 104) the subject's eye motion response thereto. FIG. 7 demonstrates the characterized eye scanning profile of an image by an illustrative subject. As shown in FIG. 7, an individual exhibits a highly distinctive eye movement pattern that can be measured for each individual. Further, multiple different types of data can be extracted from the individual's eye movement pattern, including the areas of focus, the pattern of search, times in motion, and times between motions. These data types are characteristic to individuals and can thus be used for biometric identification. For example, which items/objects in the image are scanned by the individual and the amount of time spent on an item can depend on the particular interests and skills of the individual. As another example, some people exhibit more efficient search patterns than others.

Figure 8:
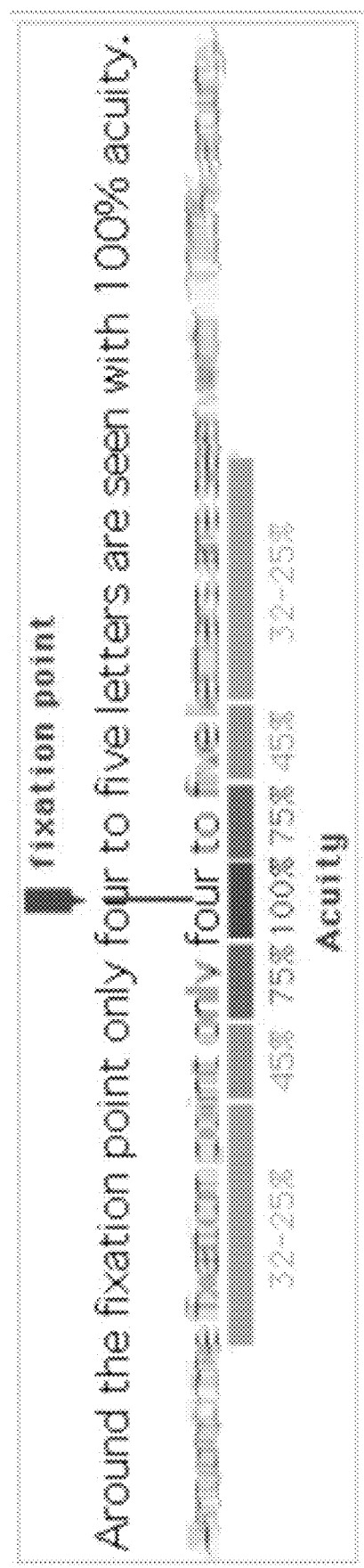
FIG. 8 illustrates a diagram demonstrating the acuity of foveal vision in reading, in accordance with an embodiment.

In some embodiments, the screening system 100 can be configured to provide text to the individual (in addition to or in lieu of an image, such as is shown in FIG. 7) and collect eye movement data as the subject reads the text. Reading is a highly specialized and structured use of vision. However, individuals' eye movement patterns can be distinctive even when performing a structured task such as reading. Even while focused on a task, the eyes' focus shifts to other places, often involuntarily. There is only a small area of detailed vision in the retina, called the fovea. The receptors in the fovea get saturated when staring at a point too long, so the eyes move to reset the receptors. FIG. 8 demonstrates the acuity of foveal vision in reading. As can be seen, only a small number (e.g., 4-5) of additional letters around the fixation point can be seen by the individual at any given time. Because individuals' foveal vision is so limited, distinctive patterns can be identified as the individuals' eyes shift focus around and from the provided text.

In some embodiments, the screening system 100 could be configured to provide video to the individual (in addition to or in lieu of an image, such as is shown in FIG. 7, or text, such as is shown in FIG. 8) and collect eye movement data as the subject watches the video. These embodiments could otherwise function similarly to the embodiments described above, particularly the image-based eye tracking embodiments.

In some embodiments, the screening system 100 can be configured to collect eye movement data for an individual in parallel with providing other tests and/or stimuli to the individual. Accordingly, the screening system 100 can obtain a large amount of information on the individual. When eye movement data is obtained in combination with other tests, these different data types can create very distinctive patterns for different individuals.

In sum, multiple different types of eye motion data (e.g., the areas of focus or fixed points in an image exhibited by the individual, the length of time the individual rests on the fixed points, various characteristics associated with the different types of eye motions, the eye movement patterns in the search, times in motion, and times between motions) could be used for biometric identification. Further, this data can be measured by providing text and/or images to the individual. Because multiple different biometric measures can be extracted from the subject's eye motion data, eye motion data has a high degree of dimensionality.

Another test that can be provided by various embodiments of the screening system 100 is a trail-making test. Trail-making tests require that the subjects draw lines from one object to the next object in the sequence until all of the objects in the sequence are connected, without any of the lines crossing. The sequences of objects could be numbers, letters, or combinations thereof. The manner in which the individual completes the trail-making test, whether the individual makes any errors, and which types of errors that the individual makes can be indicative of a variety of different conditions, including conditions that impair cognitive functions (e.g., dementia). Therefore, some embodiments of the screening system 100 could be configured to measure trail-making test data as at least one of the mechanisms for screening subjects for various conditions. However, trail-making test data can also vary from individual-to-individual. Therefore, the trail-making test data captured by the screening system 100 for screening purposes could additionally be used for biometric identification of the subject.

A typical trail-making test includes a number of different steps. First, the individual scans the screen to find the starting point. During this scanning process, the individual's eyes move rapidly, stay on a fixed point for some time, and then move to another point. This process is repeated until the whole scene has been scanned. There are several potential data points that can be extracted from the scanning process, namely, the areas of focus, the pattern of search, the times in motion, and the times between motions. As described above with respect to eye tracking, the patterns that individuals exhibit are highly individualized and can thus be used for biometric identification. Further, as noted above, even when an individual is focused on a task, their eyes tend to move to other places, often involuntarily. These eye motions are also highly individualized and can thus likewise be used for biometric identification. After the scanning process is completed, the individual moves his or her finger to the first object. This step can likewise involve many eye movements that can be tracked. The individual then finds the next object in the sequence. During this step, the individual may leave his or her finger at the previous object, raise the finger and then need to place it again, or take other actions that may be characteristic to that individual. Finally, the individual moves his or her finger to the next object. During this step, the manner in which the individual moves his or her finger, whether the individual commits an error and crosses another line, the particular path selected by the individual, and a variety of other actions could likewise be characteristic to that individual. In addition to the factors described above, the length of time to accomplish each step and the types of errors committed by the individual in performing the trail-making test also vary from individual-to-individual and, thus, could be used for biometric identification. Some errors could include whether the individual placed a finger in an incorrect place (e.g., not on an object or on an incorrect object), whether the individual started to draw to an incorrect object in the sequence (e.g., realized the error and went back to the previous object in the sequence), whether the individual crossed a previous line or connected to an incorrect object, and whether the individual stopped at any point.

Figure 9A:
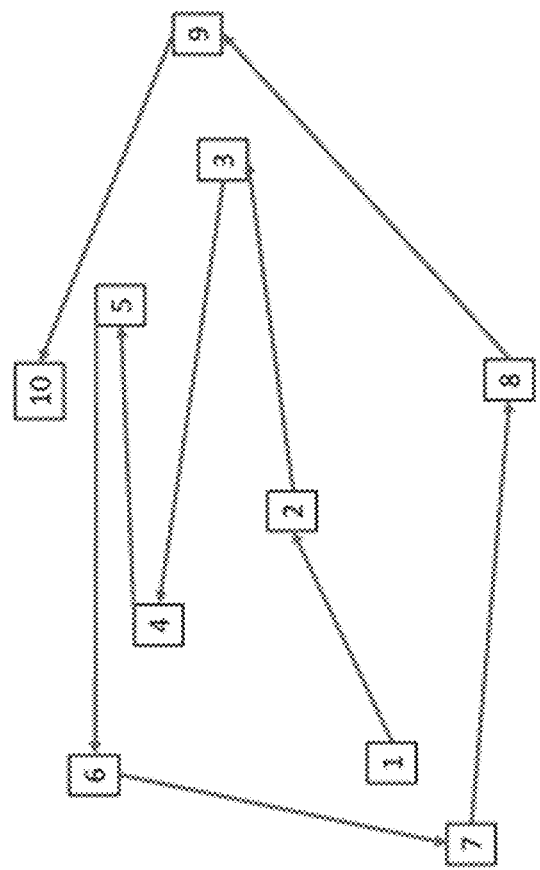
FIG. 9A illustrates a diagram of a trail making test, in accordance with an embodiment.
Figure 9B:
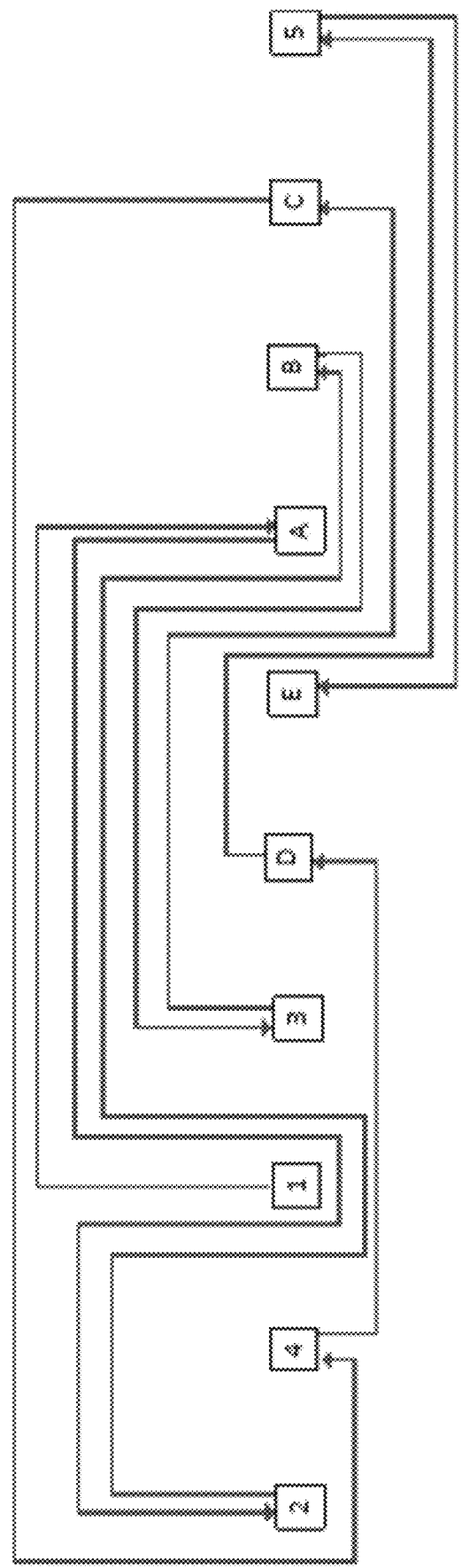
FIG. 9B illustrates a diagram of another trail making test, in accordance with an embodiment.

In some embodiments, the screening system 100 can be configured to provide a trail-making test to the subject and measure (e.g., via the visual response detector 104 or tactile response detector 102) the subject's response (i.e., the acts of performing the test, either alone or in combination with related data, such as eye movements) thereto. FIGS. 9A and 9B demonstrates various trail-making test solutions by an illustrative subject. As can be seen from FIGS. 9A and 9B, the sequential objects in the trail-making tests can be arranged in different manners and with differing degrees of complexity. Further, multiple different solutions to the trail-making tests are possible. Accordingly, individuals will complete these trail-making tests in a highly individualized fashion, which means that the data gathered from the tests will likewise be highly individualized. A variety of different types of biometric data can be extracted from an individual's performance of a trail-making test, including the length of time to complete the test or individual steps thereof, whether the individual committed any errors, which errors the individual committed, eye movement data during the performance of the test, the shapes or types of lines used to connect sequential objects, and so on. In some embodiments, the screening system 100 can further be configured to introduce distractions (e.g., noise, extraneous objects appearing and disappearing, or even moving the objects that haven't yet been connected) to the trail-making test to further increase the dimensionality of the tracked response data.

In sum, multiple different types of trail-making test response data (e.g., the length of time to complete the test or individual steps thereof, whether the individual committed any errors, which errors the individual committed, eye movement data during the performance of the test, and the shapes or types of lines used to connect sequential objects) could be used for biometric identification. Because multiple different biometric measures can be extracted from the subject's trail-making test response data, the response data has a high degree of dimensionality. Even under the same conditions, there can be variations in each of these values for an individual.

Another test that can be provided by various embodiments of the screening system 100 is a finger tapping test. A finger tapping test is essentially a more complex version of the popular arcade game Whack-A-Mole. In particular, objects appear on the screen and the subject is directed to take some specific action, such as tapping on the object the number of times specified or to ignore the object. The manner in which the individual completes the finger tapping test, whether the individual makes any errors, and which types of errors that the individual makes can be indicative for a variety of different conditions, including conditions that impair cognitive functions (e.g., dementia). Therefore, some embodiments of the screening system 100 could be configured to measure finger tapping test data as at least one of the mechanisms for screening subjects for various conditions. However, finger tapping test data can also vary from individual-to-individual. Therefore, the finger tapping test data captured by the screening system 100 for screening purposes could additionally be used for biometric identification of the subject.

In some embodiments, the screening system 100 can be configured to provide a finger tapping test to the subject and measure (e.g., via the visual response detector 104 or tactile response detector 102) the subject's response thereto. The screening system 100 can be configured to track a number of different types of response data. For example, objects could appear or disappear at the periphery of the individual's vision (e.g., as determined by tracking the individual's foveal vision as described above) to test the individual's peripheral vision. Further, the individual's response time (i.e., the time it takes for the individual to tap on a new object) can be tracked. In some embodiments, the rate at which new objects appear or disappear could be dynamic or otherwise adjusted in order to increase the dimensionality of the tracked data. Further, the accuracy in the location of the taps and whether the individual is performing the correct number of taps (i.e., the number of taps that the individual is being instructed to perform) could likewise be tracked. Because the screening system 100 could control the objects and appearance/disappearance times, a finger tapping test can be very robust, i.e., it can have a substantial amount of complexity and dimensionality. In particular, finger tapping tests allow for the measurement of the individual's eye movements, response times, hand-eye coordination skills, and motion control skills. In some embodiments, the finger tapping test could instruct individuals to tap squares once, tap triangles twice, and to not tap pentagons. The finger tapping test could then show other shapes not mentioned in the instructions (e.g., hexagons, circles, or birds), either separately or in combination as distractions. Different colored objects could also be introduced into the test to add further complexity for non-color blind individuals. Any of this data could be used for biometric identification.

In sum, multiple different types of finger tapping test response data (e.g., timing, whether the individual followed instructions or otherwise committed any errors, which errors the individual committed, and how the individual was impacted by different types of distractions) could be used for biometric identification. Because multiple different biometric measures can be extracted from the subject's finger tapping test response data, the response data has a high degree of dimensionality. Even under the same conditions, there can be variations in each of these values for an individual.

In some embodiments, the screening system 100 could be configured to use historical data for a given subject to determine variations in a subject's biometric data captured using any of the techniques described above. These determined variations can be used to determine ranges or thresholds for the various biometrics data types for a subject, which can then be used for subsequent biometric identification of the subject. Finally, the subject's historical data can be used to determine which measures and biometric data types are most useful for identification purposes of the subject. Accordingly, a biometric template or model could be developed for each subject based on his or her typical data ranges or thresholds associated with any of the various measures described above.

The various neurophysiological stimuli and testing techniques used by the screening system 100 can be powerful tools for screening individuals for particular conditions and/or biometrically identifying individuals (as discussed in further detail below) because many distinct parameters in the subject's response to the stimuli can be measured, the subject's response is dynamic, the stimuli are highly customizable (e.g., the number or rate of the test elements can be changed or distractions can be added to the stimuli) to provide different difficulties and complexities, the stimuli response data can be assessed against detailed historical result data for each subject, and the stimuli activate the subject's cognition and memory (which are some of the main factors being assessed in screening for particulars conditions, e.g., long COVID or dementia).

Dynamic Adaptive Biometrics for Screening Systems

The various embodiments of the screening system 100 described above collect a wide range of data about users, including data for the autonomic and somatic responses exhibited by users in response to the various stimuli described above. In particular, the screening system 100 records the responses each time the subject is screened, and these recorded responses can then be used to determine if the subject's responses to the stimuli have changed, which can in turn indicate that the subject may have a condition (e.g., COVID-19) that the screening system 100 is seeking to identify. Due to the sequencing of the testing performed on the subject, the nature and timing of the provided stimuli, and the variety of different features recorded, the biometric data captured by the screening system 100 has a high degree of dimensionality. The high dimensionality and the corresponding benefits of the data captured by the screening system 100 for use a biometrics is demonstrated in TABLE 1.

In particular, TABLE 1 compares some conventional biometric measures (e.g., fingerprint, retinal scan, and voiceprint) to adaptive dynamic biometric data that is captured by the screening system 100 (e.g., pupil dilation, eye motion, trail-making, and finger tapping). Fingerprints and retina scans have three dimensions: a horizontal and vertical dimension with color (e.g., black and white) at each point. Voiceprints have three dimensions: frequency, amplitude, and time. Because pupil dilation, eye motion, trail making and finger tapping are responses to the many types and number of stimuli, differing in type, shape, color, and location, along with various distractions, over time there are many dimensions.

A biometric type is considered to be "dynamic" as set forth in TABLE 1 when it provides a continuous set of data points that change over time. Pupil dilation, eye motion, and voice, can be observed continuously whatever the subject is doing, not just while a specific task is being completed, as with the other biometrics. This enables continuous testing for all types of screening, including as a new condition developing, such as illness, drowsiness or intoxication, and also determining that the individual is the same as the one previously identified, and not someone trying to replace the individual. A "dimension" as set forth in TABLE 1 constitutes the number of possible "degrees of freedom" associated with the biometric type, i.e., the number of different aspects of the biometric type that can be independently measured. Fingerprints and retina scans are static, so there are no options to change them. Therefore, their history is just the corresponding image of the fingerprint or image. Voiceprints can use a number of previously recorded phrases for identification. However, as already described, pupil dilation, eye motion, trail making, and finger tapping are dynamic responses to complex stimuli and distractions, which generates the wide range of different test conditions. This wide range of options enables a rich history to be collected and used in determining identity and other screening functions. A key reason that pupil dilation, eye motion, trail making, and finger tapping vary so widely with different stimuli and distractions is that they are heavily influenced by cognitive activity, that is the brain recognizing the many aspects of the stimuli and distractions and responding to them through these biometric measures. Fingerprints and retina scans are static and thus not affected by cognition, which voice is affected by cognition, but in a much more limited way.

As can be seen, the biometric data types captured by the screening system 100 are dynamic, can be tested in a variety of different manners using complex stimuli and distractions, can be combined with historical patient data to assist in identifying the subject, involve the use of the subject's cognition. The fact that the biometric data types captured by the screening system 100 can incorporate a variety of complex stimuli and distractions is beneficial because it allows the dimensionality of the data to be greatly increased. Namely, the screening system 100 can alter the manner in which the tests provided to the subject are performed (e.g., by adding distractions and determining how the subject on average responds to such distractions or by testing how the subject responds to different types of stimuli), which can in turn allow the screening system 100 to extract many data points with respect to all of the ways that the subject interacts with or responds to the tests. Due to the dimensionality of the data captured by the screening system 100, the screening system 100 can correspondingly use a variety of different data types for biometric identification.

TABLE 1

| Biometric Type | Dimensions | Dynamic | Continuous | Options | History | Cognition involved? |
|---|---|---|---|---|---|---|
| Fingerprint | 3 | No | No | None | Limited | No |
| Retinal scan | 3 | | | | | |
| Voiceprint | 3 | Yes | Yes | Phrases | Limited | Limited |
| Pupil dilation | Many | Yes | Yes | Complex stimuli and distractions | Extensive | Yes |
| Eye motion | | | | | | |
| Trail making | | | No | | | |
| Finger tapping | | | | | | |

TABLE 2 below provides further details on the data types captured by the screening system that are identified above in TABLE 1. As shown in TABLE 2, a variety of different measures can be extracted from various different complex stimuli or tests that the screening system 100 can provide to individuals. Further details on the types of biometric data that can be tracked in connection with these various complex stimuli or tests are described in greater detail below. However, TABLE 2 provides a brief summary of the different types of biometric measurements, the incorporation of distractions into the testing schemes, and the types of discrete stimuli that can be used in connection with the tests. In short, the biometric data that can be extracted from these types has a high degree of dimensionality because of the large number of individual biometric measurements that can be made in connection with the various tests and the fact that different stimuli and/or distractions can further be incorporated into the tests.

TABLE 2

| Task Type | Stimuli | Distractions | Measures |
|---|---|---|---|
| Pupil dilation | Smells, tastes, sounds, lights, | Sights, sounds, lights, and | Sampling times and values of continuous |

TABLE 2-continued

| Task Type | Stimuli | Distractions | Measures |
|---|---|---|---|
| Eye motion | cognitive factors (e.g., other tests) Images, videos, other tests, reality | smells (including timing and combinations of stimuli) | process Sequence, position, & timing of focus points (~3/second), fixations |
| Trail-making | Arrangement of objects, object types | | Timing, accuracy, connections, errors |
| Finger tapping | Types, locations, appearance, and timing of objects | | Delays, accuracy, misses, false taps |

As set forth below in TABLE 3, cognition or reaction-based biometric data for a subject can be captured either directly (D) or indirectly (I) by the screening tests described herein. Regardless of whether the biometric data is captured directly or indirectly by the screening tests, this data could be used for biometric identification purposes by the screening system 100.

TABLE 3

| Biometric Measure | Pupil Dilation Test | Eye Tracking Test | Trail Making Test | Finger Tapping Test |
|---|---|---|---|---|
| Eye motion | | D | | |
| Pupil dilation | D | | | |
| Scan scene | I | D | D | D |
| Identify objects | I | I | D | D |
| Read instructions | D | D | D | D |
| Speak or sing | I | D | I | I |
| Hear instructions | D | | D | D |
| Recognize distractions | D | I | D | D |
| Read out loud | I | | D | D |
| Make sounds | I | | I | I |
| Understand instructions | D | | D | D |
| Plan actions | D | | D | I |
| Remember instructions | I | | D | D |
| Remember locations | I | D | D | |
| Appropriate motions | I | D | D | D |
| Significant errors | D | D | D | D |
| Accurate actions | I | D | D | D |
| Fine motion errors | I | D | D | D |
| React to planned stimuli | D | I | I | D |
| React to surprises | D | I | D | D |
| Recognize as distraction | D | I | D | D |
| React appropriately | I | I | D | D |

In addition to the autonomic and somatic responses, the screening system 100 can also capture a wide range of other data related to the subject as part of the screening process. For example, in embodiments where the screening system 100 measures the subject's pupillary response to an olfactory stimulus, the visual response detector 104 (e.g., a camera or an image sensor) could further capture retinal data (e.g., vascular patterns and landmarks) for the subject. These measured autonomic and somatic responses and other data associated with the user could further be used for biometric identification in order to, for example, confirm the identity of the individual seeking to take the screening test or tests provided by the screening system 100. The biometric data used for user identification could include any of the information collected by the screening system 100 either prior to, during, or after any test that can be used to distinguish users from other individuals, either alone or in combination with other data. In some embodiments, the biometric data could include, for example, measurements of a user's eyes (e.g., vascular patterns and landmarks), fingerprints, arrangements of palm veins, facial recognition, palm prints, hand geometry, iris recognition, retina pupillary response to olfactory stimuli, and performance on trail-making or eye-hand coordination tests. In some embodiments, the biometric data could include data that relates to the physical characteristics of the user (e.g., retinal vascular patterns and landmarks). In some embodiments, the biometric data could include data that relates to the user's patterns that tend to distinguish the user from other individuals (e.g., the average accuracy with which the user performs trail-making tests).

As noted above, the screening system 100 can include a user identification system 109 that is configured to confirm the identity of the user or users that are interacting with the screening system 100 (e.g., are attempting to take a screening test for one of more conditions). One feature of the various embodiments of the screening system 100 described above is that the screening system 100 is collecting substantial amounts of information for a single user on a repeated (e.g., daily) basis and much of the collected information could be used as biometric data for user identification. Accordingly, various combinations of biometric data can be used as templates or models for user identification. As used herein, a "biometric template" or "biometric model" refers to a collection of features represented by biometric data that serve to uniquely identify a particular individual. Further, the screening system 100 could be configured to implement a dynamic adaptive biometric system in which the biometric templates are updated or altered (e.g., by using different combinations of types of the collected biometric data) over time. In some embodiments, the biometric templates could be updated or altered on a periodic (e.g., weekly) basis. In some embodiments, the biometric templates could be updated or altered in response to particular conditions (e.g., when a particular template has been compromised).

As generally set forth above, the screening system 100 can be used to screen for a variety of different conditions, including COVID-19. The screening system 100 thus has utility as a public health tool for tracking the spread of conditions throughout a particular population, especially in embodiments where the screening data could be combined with geographic data (e.g., obtained via the user's mobile device in embodiments where the screening system 100 includes such devices) to users' movements and potential interactions with other individuals within the population. However, an important aspect for driving this utility is to confirm the identity of the individual taking the test or tests provided by the screening system 100. Notably, if the individual taking the screening test is not who they purport to be (i.e., is not the user that the screening system 100 is associated with), then this may frustrate the ability to completely and accurately monitor the emergence and spread of conditions (e.g., COVID-19) throughout a community. Further, confirming individuals' proper identity in connection with the screening tests is important because some individuals may seek to fake a screening test or have someone else take the screening test on their behalf in order to improperly gain access to a particular location or service (e.g., gain admittance to an airport or avoid a positive result from a screening test that could affect their ability to come into work). Still further, confirming individuals' proper identity in connection with the screening tests is also important because it would be undesirable for the screening system 100 to take actions against the incorrect individual.

In some embodiments, the biometric data used by the screening system 100 for user identification could include non-invertible biometric data. Non-invertible biometric data is data for which it is computationally difficult or impossible to reconstruct the physical characteristics of the individual from which the non-invertible biometric data was generated. In other words, non-invertible biometric data cannot be reverse engineered to extract the physical profile, appearance, or characteristics of the individual. These embodiments of the screening system 100 can be beneficial because the non-invertability of the biometric data can provide improved data security. In some embodiments, the screening system 100 can be configured to convert invertible biometric data that has been captured into a non-invertible format.

Figure 10:
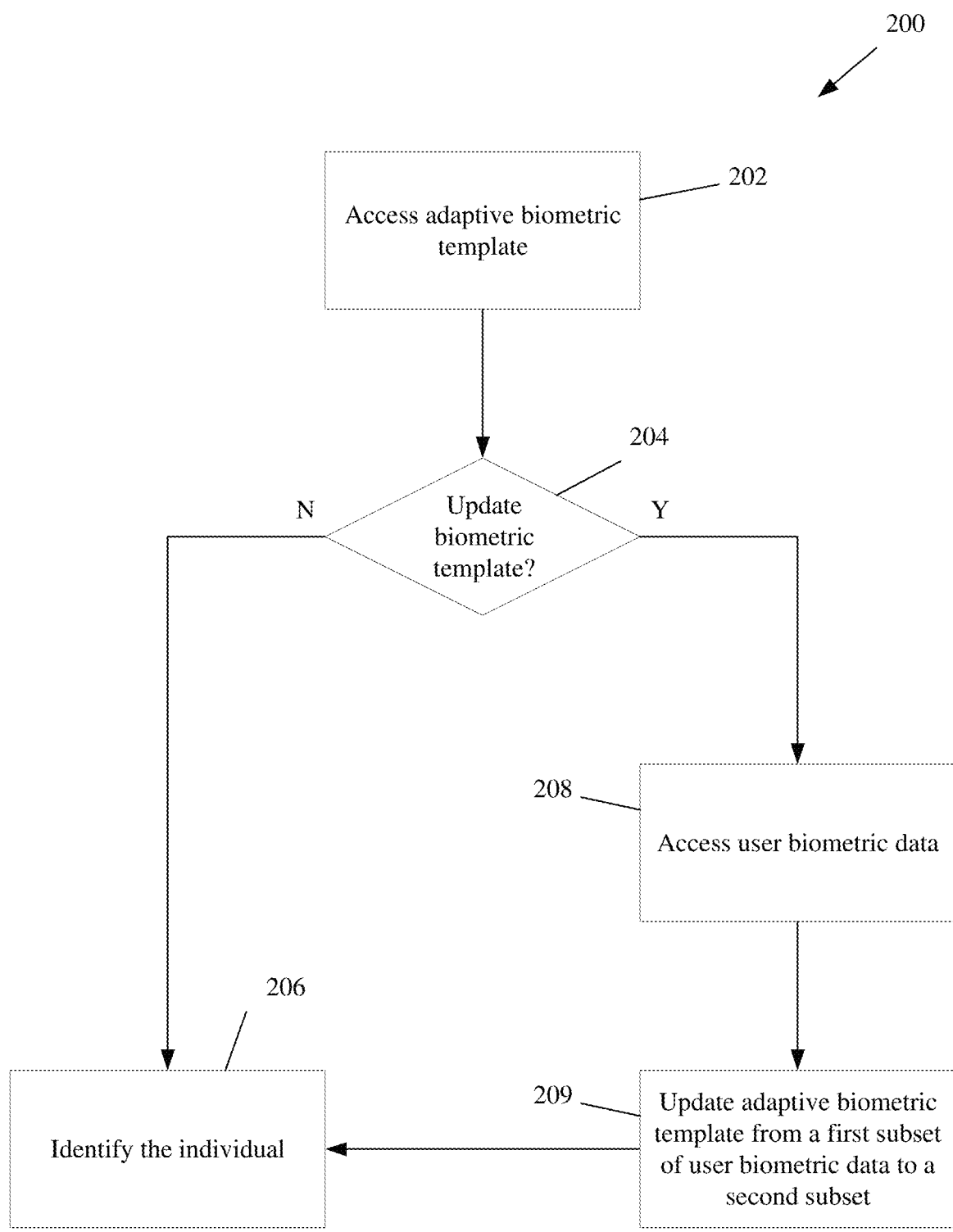
FIG. 10 illustrates a flow diagram of a process executed by a screening system for identifying a subject using a dynamic adaptive biometric, in accordance with an embodiment.

In sum, the screening system 100 captures significant amounts and different types of data for each user. Due to the nature of the data that is collected by the screening system 100 for the screening tests, the collected data can be used as a biometric for identifying the individual that is intended to be the subject of the tests (in some instances, referred to as the "user"). In particular, the screening system 100 can be configured to make use of non-invertible biometric data. Further, the screening system 100 only requires a subset of the collected data in order to identify the user because of the amount of and the variation in the collected data. Therefore, these factors can be leveraged to use a dynamic adaptive biometric scheme that can create biometric identification templates based on a subset of the collected biometric data and dynamically update the biometric templates to use different combinations of biometric data to identify individuals in response to various triggers or changing conditions. One embodiment of such a process 200 is shown in FIG. 10. In one embodiment, the illustrated process 200 can be embodied as computer-executable instructions stored in a memory (e.g., the memory 108) that, when executed by a processor (e.g., the processor 106), cause the screening system 100 to execute the described process 200 and/or steps thereof. In one embodiment, the process 200 can be executed, at least in part, by the user identification system 109.

In some embodiments, the process 200 can be initiated upon or in response to a user logging into a software application being executed by the screening system 100, beginning a screen test, or taking other actions with respect to the screening system 100 for which the user's identity needs to be verified. Accordingly, the screening system 100 accesses 202 the biometric template associated with the particular user for the screening system 100 and determines 204 whether the biometric template needs to be updated. In one embodiment, the biometric template could be stored in the database 110 and retrieved by the screening system 100 as needed. In another embodiment, the biometric template could be stored in the memory 108 of the screening system 100. In some embodiments, the screening system 100 can determine 204 that the biometric template needs to be updated if a particular threshold time period has elapsed from the last time that the biometric template was updated. In other words, the screening system 100 can periodically update the user's biometric template. In other embodiments, the screening system 100 can determine 204 that the biometric template needs to be updated if a trigger condition has been satisfied. For example, the screening system 100 could determine 204 that the biometric template needs to be updated if the particular combination of biometric features used in the template has been compromised or has otherwise been reduced in effectiveness.

In one embodiment, the screening system 100 could be programmed to determine which biometric types are particularly distinguishable for each individual, particularly which biometric types are able to distinguish each individual from other individuals in their cluster. In the event that the screening system 100 determines that there is a need to identify biometrics that will distinguish a particular individual from others (e.g., other individuals in the same cluster), the screening system 100 can take a variety of different actions. In one embodiment, the screening system 100 can administer biometric tests that look for the boundary (or envelope) of this subject's capabilities in relation to others. For example, if the individual is very good at trail-making tests, the screening system 100 can make those tests "harder" (e.g., provide more objects, provide more complex arrangements of objects, provide different varieties of distractions, or increase the rate at which objects appear or disappear), until the subject begins to fail the trail-making tests. In another embodiment, the screening system 100 could use different scenes that incorporate the individual's interests or knowledge. As noted above, the eyes will tend to spend more time and come back more frequently to objects of particular interest. Accordingly, biometric tests could be personalized for each individual by customizing the surrounding scene to be specific to that individual. For example, if an individual has an interest in surfing, a surfing scene could be incorporated into the biometric test. As such, other individuals (who presumably are not interested in surfing) would not exhibit the same biometric characteristics because their eyes will not linger on the objects in the scene for which they are not interested. In another embodiment, the screening system 100 can switch to a different biometric.

In some embodiments, the screening system 100 can further be configured to change the biometric template for the individual in response to a variety of different events other than the biometric template becoming compromised, including the individual aging or suffering a medical condition (e.g., a stroke).

In some embodiments, the biometric template can make use of biometrics that require that the user interact with the screening system 100 in some manner for the biometric data of the individual to be collected. In these embodiments, the screening system 100 could prompt the user to take the necessary actions for the user's biometric data to be collected. For example, in an embodiment where the screening system 100 uses retinal vascular patterns and landmarks as a biometric, the screening system 100 could prompt the user to have their eyes scanned (e.g., by the visual response detector 104 or a camera). As another example, in an embodiment where the screening system 100 uses trail-making test accuracy as a biometric, then screening system 100 could provide the user with the requisite trail-making test and prompt the user to complete the test. These steps of having the screening system 100 collect the necessary biometrics could occur prior to or in conjunction with the screening system 100 accessing 202 the user's biometric template.

In some embodiments, the screening system 100 could make use of different biometrics depending on various characteristics associated with the individual. For example, if the subject is blind, the screening system 100 could make use of audio-based biometrics instead of visual-based biometrics. As another example, if the subject has difficulties with fine motor control (e.g., has suffered from a stroke), the screening system 100 could avoid using trail-making tests or other tests requiring fine motor control. Alternatively, the screening system 100 could customize the tests to address the particular subject's issues (e.g., adjust the trail-making test to require only gross motor control to succeed).

If the screening system 100 determines 204 that the user's biometric template does not need to be updated, the screening system 206 can proceed to identify 206 and confirm the identity of the individual interacting with the screening system 100. If the screening system 100 determines 204 that the user's biometric template does need to be updated, the screening system 206 can proceed to access 208 the biometric data that has been collected by the screening system 100 for the user (e.g., from previous instances of screening tests) and update 209 the biometric template. In one embodiment, the screening system 100 can be programmed to update the biometric template from a first subset of the user biometric data to a second subset of the user biometric data. As one illustrative example, the biometric data collected by the screening system 100 included retinal vascular characteristics, facial recognition, and trail-making test accuracy. In this example, the biometric template could include a combination of retinal vascular characteristics and trail-making test accuracy. Further, the screening system 100 could determine 204 that the biometric template should be updated and adjust the biometric template to instead use a combination of facial recognition and trail-making test accuracy. In this way, the screening system 100 is able to dynamically update the biometric template used for identification as necessary. Accordingly, the screening system 100 can proceed to identify 206 and confirm the identity of the individual interacting with the screening system 100 using the updated biometric template.

In some embodiments, the screening system 100 can be programmed to flag the individual based on whether the individual is properly identified and the results of the screening test performed thereby. The flag can in turn be used as part of an access control system. In other words, the individual could be flagged in order to control the individual's ability to access various locations or services. For example, an individual could be flagged to control whether he or she can access an airport or be admitted onto a flight. As another example, an individual could be flagged to control whether they are allowed to go into work or not. In one illustrative example, the screening system 100 could control the status of a COVID-19 access control flag based on the results of a COVID-19 screening test administered by the screening system 100 and a confirmation of the individual's identity. Access control flags could be particularly beneficial in the context of COVID-19 or other infectious diseases because individuals may have particular incentives to falsify the results of the screening tests.

Figure 11:
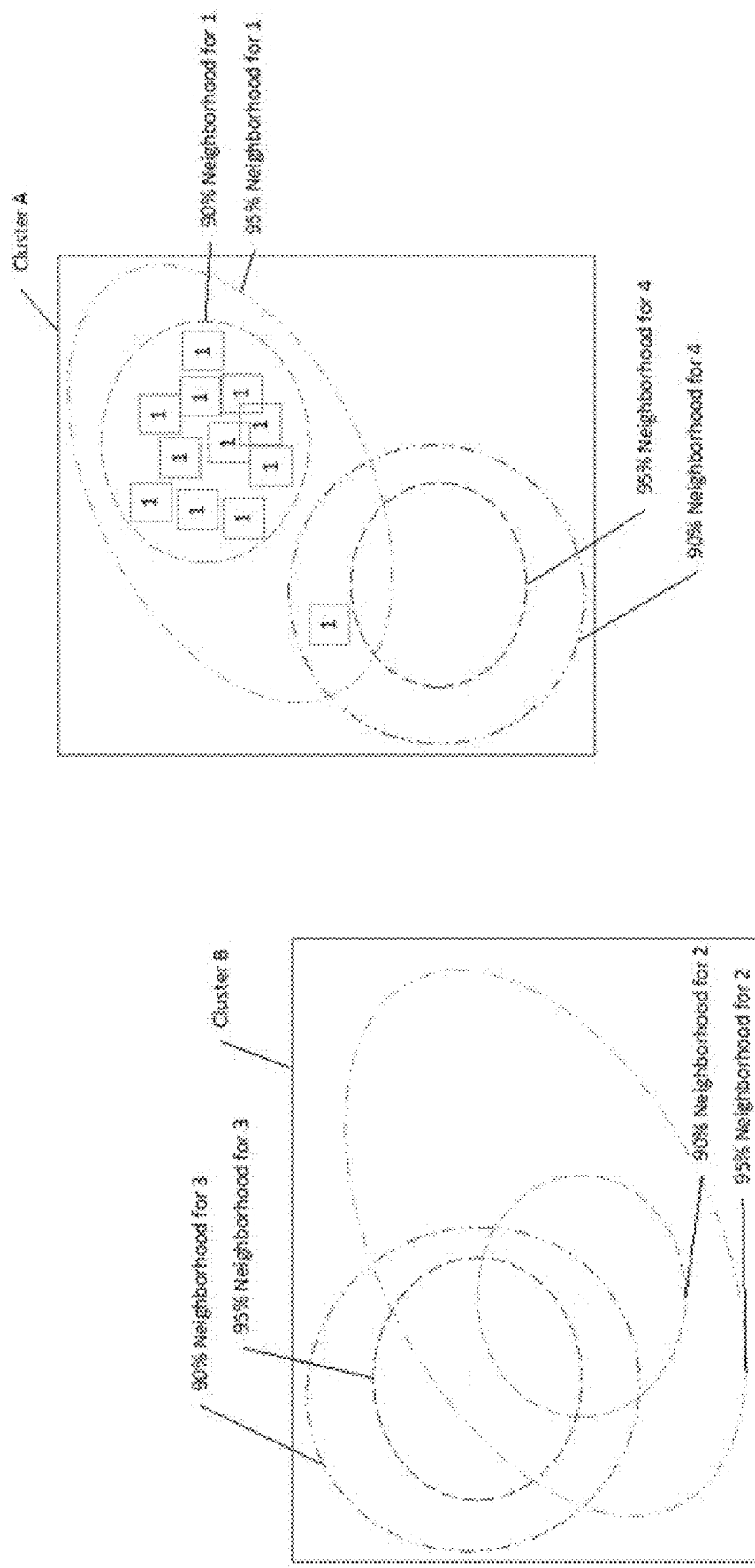
FIG. 11 illustrates a diagram of a clustering technique for comparing biometric data, in accordance with an embodiment.

The screening system 100 can be programmed to use a variety of different techniques or algorithms to perform the identification 206 of the individual interacting with the screening system 100. In one embodiment, the screening system 100 could use a clustering algorithm to perform the identification 206. Referring now to FIG. 11, there is shown a diagram showing an illustrative clustering technique. In particular, one paradigm is to think of the N measures from an identification test as creating an N-dimensional space. A single test thus creates a point in the N-dimensional space. The set of points for an individual taking the same test many times creates a neighborhood in this space. With a sufficient number of tests, the probabilities associated with particular points or regions in the space could be estimated. The results from a subsequent test could then be used to generate a probability that they correspond to a particular individual by examining the probability neighborhoods in the space for that individual. Similarly, the results of a test can generate probabilities that they match the probability neighborhoods of other individuals.

As shown in FIG. 11, the points marked "1" represent the hypothetical results for individual 1 taking a particular test several times (plotted in N-dimensional measure space, but shown here in two dimensions for ease of visualization). Most of the points are clustered in a small area, with one outlier. Accordingly, neighborhoods can be defined in this measure space. In this particular example, the inner neighborhood contains 90% of the test results for individual 1 for this test. We could further estimate a larger neighborhood which would contain 95% of the test results for individual 1. Subsequent test results could be mapped to the N-dimensional spaces and be compared to the various probability neighborhoods to determine which individual(s) the test results could correspond to. If the results for the individual being tested correspond to the subject that the screening system 100 is intended to be testing, the screening system 100 can thereby identify 206 the individual.

Further, a variety of different clusters for seeking to identify different individuals could be developed. For example, it can be seen in FIG. 11 that it is very unlikely that a test result for individuals 2 or 3 would overlap with the test results for individual 1 because individual 1 resides within a different cluster than individuals 2 and 3. For individual 4, there is a small probability (i.e., less than 5%) that a test result would overlap with individual 1. Clusters can also be used to simplify the process of checking for overlaps in test results. A cluster is a region of N-space for a particular test. The cluster also describes a set of individuals with nearby neighborhoods in N-space for a particular test. In this particular example, cluster A contains individuals 1 and 4, and cluster B contains individuals 2 and 3. If a test result appears in the region of cluster A, then individuals 1 and 4 need to be considered, whereas individuals 2 and 3 can be ignored as possibilities.

In one embodiment, the described clustering technique could also be used to generate alerts for subjects. For example, the outlying result for individual 1 shown in FIG. 11 might correspond to a problem that the individual had at the time they took the test, such as being intoxicated or having COVID-19. Accordingly, the screening system 100 could generate an alert that the individual exhibited outlier conditions and may need to seek medical evaluation. In some embodiments, the screening system 100 could further prompt the subject to input the reason behind the outlier results, if known, either contemporaneously with the alert or sometime thereafter. This could be beneficial because such data could be useful for the screening system 100 to have for future reference, such as assisting in identifying future instances of the condition.

In instances where the screening system 100 determines that the individual interacting with the system 100 is not the proper user or the screening system 100 cannot otherwise confirm the identity of the individual, the screening system 100 can be configured to take a variety of different actions. In some embodiments, the screening system 100 could prevent the individual from taking the screening test or void the results of any test that has been taken. In some embodiments, the screening system 100 could contact relevant authorities that an individual is attempting to improperly take screening tests using another user's credentials.

It should additionally be noted that although the steps of the process 200 are depicted as being performed in a particular order, this embodiment is simply for illustrative purposes. For example, the steps of the process 200 can be executed in a different order or simultaneously. All such modifications of the process 200 fall within the scope of this disclosure.

In some embodiments, the screening system 100 can be configured to modify the biometric template when a particular template is determined to have been compromised. For example, the screening system 100 could adjust the biometric tests to be customized for the user (e.g., make the tests harder or personalize the scene associated with the test to the particular individual). These and other techniques for modifying the biometric template are discussed further above.

Figure 12:
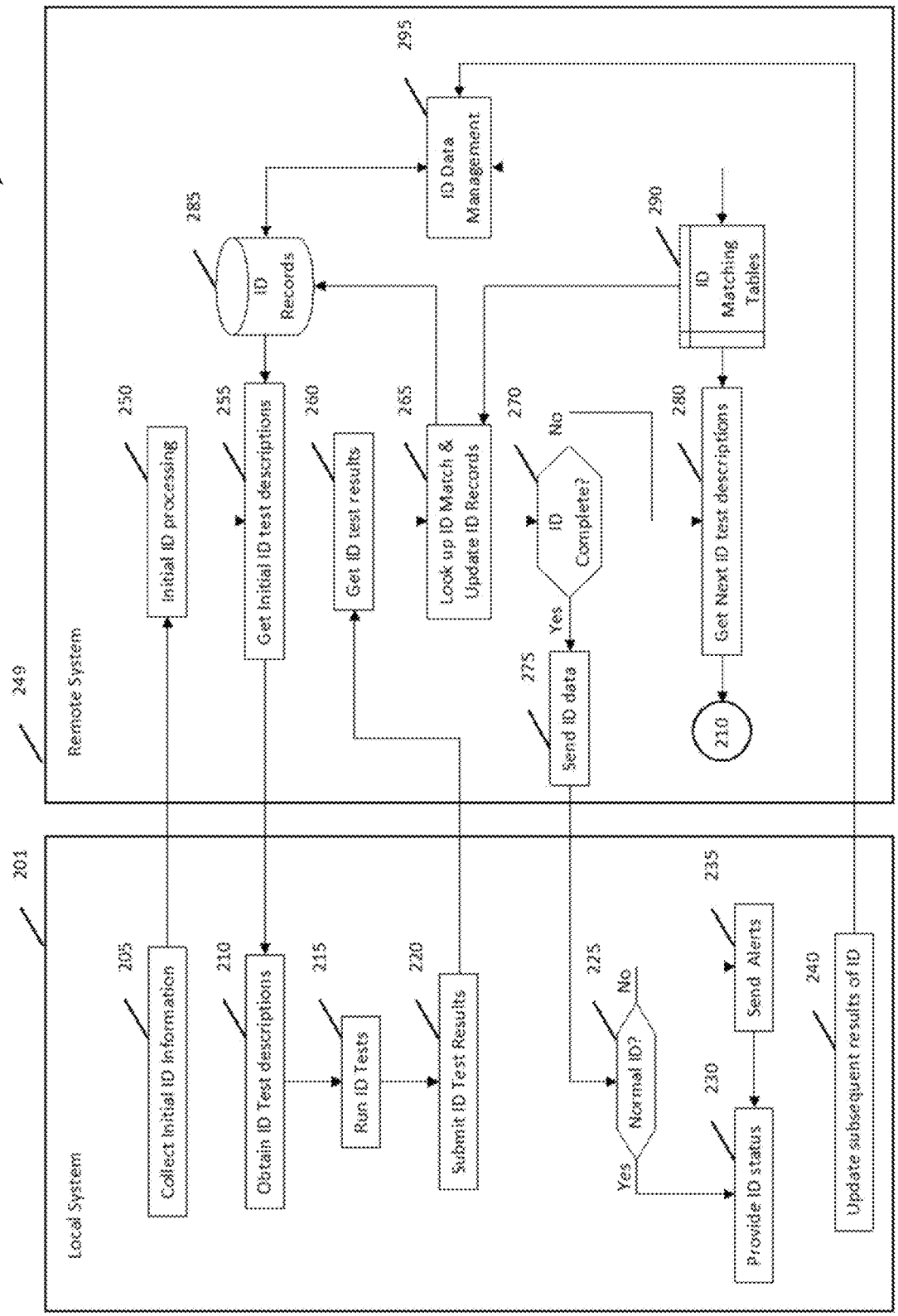
FIG. 12 illustrates a flow diagram of another process executed by a screening system for identifying a subject using a dynamic adaptive biometric, in accordance with an embodiment.

In one embodiment, systems, such as the screening system 100 described above, can be configured to execute various processes for identifying individuals. Another example of such a process 300 is shown in FIG. 12. In one embodiment, the operation of the screening system 100 is divided into a Local Device 201 and a Remote Processing system 249. The Remote Processing system 249 can be implemented in a single physical system, or it can be distributed across many systems, for example in a cloud computing environment.

In this embodiment, the process 300 starts by collecting initial ID information 205. The screening system 100 can adapt to different situations and can be used in several ways. For example, as part of a login process, an individual may be using their own smart device or only a few people might use that device (because many smart devices use fingerprints or face recognition). In other examples, an identification of the individual can be obtained by other means, such as providing an additional factor in conjunction with a conventional identification system (e.g., via login and password or an ID card). In yet other examples, no other identification information may be available. In this case a simple biometric, such as an image of the face of the individual, may be collected as a preliminary identification in the recognition process. Some forms of identification may not be available, for example due to injury or being unconscious, so whatever is available can be used, such as a photograph of a hand.

The initial ID information can be sent to Initial ID processing 250 in the Remote Processing system 249. The Initial ID processing 250 function determines the mode of operation and performs any conversions to internal system formats, such as converting photographs to standard ID formats. The system uses this information to look up initial ID test descriptions 255 from the ID Records database 285.

The ID test descriptions 210 are sent to the Local Device 201. The ID tests 215 are run with the individual. The results of the tests 220 are submitted 260 to the Remote Processing 249. The identification data gathered so far is used to access the ID Match Tables 290 to determine the status of the identification. The ID Records 285 are updated 265.

A somewhat different mode of operation may be performed for some kinds of ID tests 215, such as pupil dilation and eye tracking, to run for long periods of time or even continuously. These tests can be set with criteria to determine when they send a report 220, for example a periodic report or a report when some threshold is passed. For example, a report 220 may be sent when the pupils are partially obscured or the eye motion slows or stops, which could occur if the individual is falling asleep, or the eyes are looking off to the side for too long a period, which could occur if the individual is distracted from the current task.

The Remote Processing system 249 checks to see if the ID process is complete 270. If the process is not complete, the Remote Processing system 249 obtains the next test(s) to be run 280 from the ID matching tables 290. This information is sent to the Local Device 210. The testing and identification process continue as described above until the ID process is complete and ID data 275 is sent to the Local Device 210 to decide what to do next 225.

Depending on how the ID system is being used, many next steps are possible. If the individual matches the ID tests, the ID status is returned to the Local Device 210 as normal 230. The Local Device 210 then takes appropriate action, such as completing the login process or verifying the individual's ID to another process or system.

However, if the ID status is not normal the Local Device 210 can send appropriate alerts 235 and report the ID status 230. Several outcomes are possible in this case. For example, the individual may not be in the ID system, the individual may definitely not match the identity claimed in the initial ID information, such as a login, the tests may not be able to give a definitive answer (for example, the results may overlap with other individuals), or the test results may be outside the normal range for one or more of the tests.

If the individual matches the identity claimed in the initial ID information, but one or more test results are outside the normal range, another application of the process may result. For example, this may be an indication of a disease, such as COVID-19, or a condition, such as intoxication. Some of the adaptive dynamic biometric tests may be the same as used for other purposes, such as described in U.S. Pat. No. 11,083,405 and U.S. patent application Ser. No. 17/528,417, which are incorporated by reference herein above.

The alerts 235 may be sent to different locations depending on the situation. For example, the individual may simply need to log in again or perform other actions as determined by a login process. In the case of security identification, an alert may go to security authorities. In the case of a health issue, alerts may go to the individual, their health representative, and/or health authorities. In the case of an incapability issue, an alert might go to appropriate authorities and access to a system requiring the capabilities in question may be denied.

A follow-up activity of updating subsequent results of the ID 240 process to the ID Data management 295 function can add information and improve the identification process. For example, if the individual was not in the ID database, they may be directed to the new individual registration process. Alternatively, if a potential health issue was indicated, subsequent medical tests indicating the status (e.g., did the individual have COVID-19 or were they intoxicated?) may be performed. In yet another case, if the identity was uncertain, a determination may be made as to whether the tested individual was the purported individual or not.

ID Data Management 295 is an ongoing process. As new information (e.g., new test results, identifications, subsequent results, new individuals, and/or new tests) becomes available to the system, the ID records 285 and ID Matching Tables 290 need to be updated. In particular, the ID Matching Tables 290 need to be optimized for fast and efficient operation of the overall system. This process can improve all aspects of system operation, including the number of tests needed to identify each individual, the time required for identification, the accuracy of identification, and resource requirements.

While various illustrative embodiments incorporating the principles of the present teachings have been disclosed, the present teachings are not limited to the disclosed embodiments. Instead, this application is intended to cover any variations, uses, or adaptations of the present teachings and use its general principles. Further, this application is intended to cover such departures from the present disclosure as come within known or customary practice in the art to which these teachings pertain.

In the above detailed description, reference is made to the accompanying drawings, which form a part hereof. In the drawings, similar symbols typically identify similar components, unless context dictates otherwise. The illustrative embodiments described in the present disclosure are not meant to be limiting. Other embodiments may be used, and other changes may be made, without departing from the spirit or scope of the subject matter presented herein. It will be readily understood that various features of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various features. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein are generally intended as "open" terms (for example, the term "including" should be interpreted as "including but not limited to," the term "having" should be interpreted as "having at least," the term "includes" should be interpreted as "includes but is not limited to," et cetera). While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups.

In addition, even if a specific number is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, et cetera" is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, et cetera). In those instances where a convention analogous to "at least one of A, B, or C, et cetera" is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, et cetera). It will be further understood by those within the art that virtually any disjunctive word and/or phrase presenting two or more alternative terms, whether in the description, sample embodiments, or drawings, should be understood to contemplate the possibilities of including one of the terms, either of the terms, or both terms. For example, the phrase "A or B" will be understood to include the possibilities of "A" or "B" or "A and B."

In addition, where features of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, et cetera. As a non-limiting example, each range discussed herein can be readily broken down into a lower third, middle third and upper third, et cetera. As will also be understood by one skilled in the art all language such as "up to," "at least," and the like include the number recited and refer to ranges that can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

The term "about," as used herein, refers to variations in a numerical quantity that can occur, for example, through measuring or handling procedures in the real world; through inadvertent error in these procedures; through differences in the manufacture, source, or purity of compositions or reagents; and the like. Typically, the term "about" as used herein means greater or lesser than the value or range of values stated by $1/10$ of the stated values, e.g., ±10%. The term "about" also refers to variations that would be recognized by one skilled in the art as being equivalent so long as such variations do not encompass known values practiced by the prior art. Each value or range of values preceded by the term "about" is also intended to encompass the embodiment of the stated absolute value or range of values. Whether or not modified by the term "about," quantitative values recited in the present disclosure include equivalents to the recited values (e.g., variations in the numerical quantity of such values that can occur, but would be recognized to be equivalents by a person skilled in the art).

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

The functions and process steps herein may be performed automatically or wholly or partially in response to user command. An activity (including a step) performed automatically is performed in response to one or more executable instructions or device operations without user direct initiation of the activity.

What is claimed is:

1. A computer-implemented method for biometrically identifying an individual via a screening system for screening a subject for a response to neurophysiological stimuli as an indication for COVID-19, wherein the screening system is configured to capture biometric data associated with the subject during screening of the subject, the biometric data comprising a plurality of biometric data types, the method comprising:
receiving ID information associated with the subject;
providing the subject a neurophysiological stimulus selected for clinical manifestations of COVID-19, wherein the biometric data associated with the subject comprises responses exhibited by the subject to previous provisions of the neurophysiological stimulus;
in connection with providing the neurophysiological stimulus, receiving, by a mobile device, a biometric template associated with the ID information, wherein the biometric template is configured to identify the subject, wherein the biometric template comprises a first subset of the biometric data for the subject captured by the screening system, the first subset comprising one or more of the plurality of biometric data types;
determining, by the mobile device, whether to update the biometric template;
in response to a determination to update the biometric template, generating, by the mobile device, an updated biometric template associated with the subject, wherein the updated biometric template is configured to identify the subject, wherein the updated biometric template comprises a second subset of the biometric data for the subject captured by the screening system, wherein the second subset comprises a different combination of the plurality of biometric data types than the first subset; and
determining, by the mobile device, whether an individual is the subject based on the updated biometric template and a response exhibited by the subject to the neurophysiological stimulus.

2. The method of claim 1, further comprising:
in response to a determination that the individual is the subject based on the updated template:
providing a stimulus to the subject;
measuring, via a detector of the mobile device, a response of the subject to the stimulus;
comparing, by a processor of the mobile device, the measured response to a reference;
determining, by the processor, whether the subject demonstrates a diminished or an absent response to the stimulus according to whether the measured response differs from the reference by a threshold; and
providing, by the processor, an alert according to whether the subject has the diminished or the absent response to the stimulus, wherein the alert comprises an intervention associated with COVID-19.

3. The method of claim 2, wherein the stimulus comprises at least one of an olfactory stimulus, an audio stimulus, or a visual stimulus.

4. The method of claim 2, wherein the stimulus comprises at least one of a trail-making test or a finger tapping test.

5. The method of claim 1, wherein the biometric data comprises at least one of eye movement data, response timing data, or accuracy data.

6. The method of claim 1, further comprising:
voiding results of a screening test provided by the screening system in response to a determination that the individual is not the subject based on the updated biometric template.

7. The method of claim 1, further comprising:
transmitting an alert to an authority in response to a determination that the individual is not the subject based on the updated biometric template.

8. The method of claim 1, further comprising:
flagging the individual with a COVID-19 access control flag in response to a first determination that the individual is the subject based on the updated biometric template and a second determination that the individual has a diminished or an absent response to the neurophysiological stimulus based on the response exhibited by the subject.

9. A system for screening a subject for a response to neurophysiological stimuli as an indication for COVID-19, the biometric data comprising a plurality of biometric data types, the system comprising:
a mobile device comprising:
a processor, and
a memory coupled to the processor, the memory storing instructions that, when executed by the processor, cause the mobile device to:
receive ID information associated with the subject;
provide the subject a neurophysiological stimulus selected for clinical manifestations of COVID-19, wherein the biometric data associated with the subject comprises responses exhibited by the subject to previous provisions of the neurophysiological stimulus;
in connection with providing the neurophysiological stimulus, receive a biometric template associated with the subject, wherein the biometric template is configured to identify the ID information, wherein the biometric template comprises a first subset of the biometric data for the subject captured by the screening system, the first subset comprising one or more of the plurality of biometric data types;
determine whether to update the biometric template;
in response to a determination to update the biometric template, generate an updated biometric template associated with the subject, wherein the updated biometric template is configured to identify the subject, wherein the updated biometric template comprises a second subset of the biometric data for the subject captured by the screening system, wherein the second subset comprises a different combination of the plurality of biometric data types than the first subset; and
determine whether an individual is the subject based on the updated biometric template and a response exhibited by the subject to the neurophysiological stimulus.

10. The system of claim 9, wherein the memory stores further instructions that, when executed by the processor, cause the mobile device to:
in response to a determination that the individual is the subject based on the updated template:
provide a stimulus to the subject;
measure, via a detector of the mobile device, a response of the subject to the stimulus;
compare the measured response to a reference;
determine whether the subject demonstrates a diminished or an absent response to the stimulus according to whether the measured response differs from the reference by a threshold; and provide an alert according to whether the subject has the diminished or the absent response to the stimulus, wherein the alert comprises an intervention associated with COVID-19.

11. The system of claim 10, wherein the stimulus comprises at least one of an olfactory stimulus, an audio stimulus, or a visual stimulus.

12. The system of claim 10, wherein the stimulus comprises at least one of a trail-making test or a finger tapping test.

13. The system of claim 9, wherein the biometric data comprises at least one of eye movement data, response timing data, or accuracy data.

14. The system of claim 9, wherein the memory stores further instructions that, when executed by the processor, cause the mobile device to:

void results of a screening test provided by the screening system in response to a determination that the individual is not the subject based on the updated biometric template.

15. The system of claim 9, wherein the memory stores further instructions that, when executed by the processor, cause the mobile device to:

transmit an alert to an authority in response to a determination that the individual is not the subject based on the updated biometric template.

16. The system of claim 9, wherein the memory stores further instructions that, when executed by the processor, cause the mobile device to:

flag the individual with a COVID-19 access control flag in response to a first determination that the individual is the subject based on the updated biometric template and a second determination that the individual has a diminished or an absent response to the neurophysiological stimulus based on the response exhibited by the subject.

17. The method of claim 1, wherein determining whether to update the biometric template comprises:

determining whether a threshold time period has elapsed from a prior update to the biometric template.

18. The method of claim 1, wherein determining whether to update the biometric template comprises:

determining whether the one or more of the plurality of biometric data types used for the first subset for identifying the subject has been compromised.

19. The system of claim 9, wherein the memory stores further instructions that, when executed by the processor, cause the mobile device to:

determine whether a threshold time period has elapsed from a prior update to the biometric template to determine whether to update the biometric template.

20. The system of claim 9, wherein the memory stores further instructions that, when executed by the processor, cause the mobile device to:

determine whether the one or more of the plurality of biometric data types used for the first subset for identifying the subject has been compromised to determine whether to update the biometric template.

* * * * *